United States Patent
Ornstein et al.

(10) Patent No.: US 7,670,798 B2
(45) Date of Patent: Mar. 2, 2010

(54) AUTOMATED METHOD AND REAGENT THEREFOR ASSAYING BODY FLUID SAMPLES SUCH AS CEREBROSPINAL FLUID (CSF)

(75) Inventors: Leonard Ornstein, White Plains, NY (US); Gena Fischer, Harrington Park, NJ (US); David Zelmanovic, Monsey, NY (US); Pamela Elsins, Wappinger Falls, NY (US); Jolanta Kunicka, Tarrytown, NY (US); Michael J. Malin, South Nyack, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1544 days.

(21) Appl. No.: 10/442,706

(22) Filed: May 20, 2003

(65) Prior Publication Data

US 2003/0215890 A1 Nov. 20, 2003

Related U.S. Application Data

(60) Provisional application No. 60/381,852, filed on May 20, 2002.

(51) Int. Cl.
*G01N 1/00* (2006.01)
*G01N 7/00* (2006.01)
*G01N 31/00* (2006.01)
*G01N 33/48* (2006.01)
*G01N 33/546* (2006.01)

(52) U.S. Cl. ............... 435/40.5; 435/1.1; 435/2; 435/243; 436/8; 436/43; 436/63; 436/148; 436/176; 436/518; 436/519; 436/520; 436/521

(58) Field of Classification Search ............ 424/70.13, 424/70.19, 70.21, 70.22, 70.27, 70.31; 435/2, 435/4, 7.24, 7.25, 30, 40.51, 112, 283.1, 435/286.5, 335, 379; 436/43, 130, 164, 172, 436/174, 519, 520, 521; 514/694

See application file for complete search history.

(56) References Cited

U.S. PATENT DOCUMENTS

| | | | |
|---|---|---|---|
| 3,741,875 A | 6/1973 | Ansley et al. | |
| 4,412,004 A | 10/1983 | Ornstein et al. | |
| 4,575,490 A | 3/1986 | Ornstein et al. | |
| 4,735,504 A | 4/1988 | Tycko | |
| 5,045,472 A | 9/1991 | Ornstein et al. | |
| 5,350,695 A | 9/1994 | Colella et al. | |
| 5,360,739 A | 11/1994 | Fan et al. | |
| 5,411,897 A | 5/1995 | Harvey et al. | |
| 5,422,277 A * | 6/1995 | Connelly et al. | ............ 436/10 |
| 5,438,003 A | 8/1995 | Colella et al. | |
| 5,633,167 A | 5/1997 | Fan et al. | |
| 5,691,316 A * | 11/1997 | Agrawal et al. | ............ 514/44 |
| 5,817,519 A | 10/1998 | Zelmanovic et al. | |
| 5,888,752 A | 3/1999 | Malin et al. | |
| 6,025,201 A | 2/2000 | Zelmanovic et al. | |
| 6,271,035 B1 * | 8/2001 | Deka et al. | ............ 436/10 |

OTHER PUBLICATIONS

A. El Rossi et al., Chromatographia, Feb. 1982, 15: 75-82.
Kaminski et al., J. Amer. Oil Chem. Soc., Aug. 1979, 56: 771-774.
D.H. Tycko et al., Appl. Optics, May 1985, 24: 1355-1365.
S. Takano et al., J. Amer. Oil Chem. Soc., Apr. 1977, 54: 139-143.
S. Takano et al., J. Amer. Oil Chem. Soc., Nov. 1977, 54: 484-486.

* cited by examiner

*Primary Examiner*—Mark Navarro
*Assistant Examiner*—JaNa Hines
(74) *Attorney, Agent, or Firm*—Harold Wells

(57) ABSTRACT

The present invention describes semi- and fully-automated methods and reagents therefor for the assay and analysis of body fluid samples, particularly non-blood samples. The methods and reagents are especially useful for the assay and analysis of cerebrospinal fluid (CSF) samples. The reagent compositions sphere and fix all cells in the sample in suspension. Reported results can include red blood cell (RBC) and white blood cell (WBC) counts, WBC differential values, cell-by-cell volumes and dry-mass concentrations.

29 Claims, 14 Drawing Sheets

| Cell Type (FIG. 11A) | ADVIA 120® Results in Cells/µL | Manual Results in Cells/µL |
|---|---|---|
| WBC | 1 | 1 |
| RBC | 1 | 0 |
| Neuts | 0 | 0 |
| Lymphs | 1 | 1 |
| Monos | 0 | 0 |
| PMN | 0 | 0 |
| MN | 1 | 1 |

| Cell Type (FIG. 11C) | ADVIA 120® Results in Cells/µL | Manual Results in Cells/µL |
|---|---|---|
| WBC | 6 | 8 |
| RBC | 23 | 22 |
| Neuts | 1 | 1 |
| Lymphs | 3 | 3 |
| Monos | 2 | 4 |
| PMN | 1 | 1 |
| MN | 5 | 7 |

| Cell Type<br>(FIG. 11E) | ADVIA 120® Results in<br>Cells/µL | Manual Results in<br>Cells/µL |
|---|---|---|
| WBC | 23 | 26 |
| RBC | 45 | 51 |
| Neuts | 0 | 0 |
| Lymphs | 22 | 25 |
| Monos | 1 | 1 |
| PMN | 0 | 0 |
| MN | 23 | 26 |

| Cell Type (FIG. 11G) | ADVIA 120® Results in Cells/µL | Manual Results in Cells/µL |
|---|---|---|
| WBC | 125 | 119 |
| RBC | 1 | 0 |
| Neuts | 0 | 0 |
| Lymphs | 118 | 113 |
| Monos | 7 | 5 |
| PMN | 0 | 0 |
| MN | 125 | 119 |

AUTOMATED METHOD AND REAGENT THEREFOR ASSAYING BODY FLUID SAMPLES SUCH AS CEREBROSPINAL FLUID (CSF)

RELATED APPLICATIONS

This application is related to U.S. Provisional Application Ser. No. 60/381,852 filed May 20, 2002, to which benefit is claimed under 35 U.S.C. §119(e)(1), and which is hereby incorporated herein by reference in its entirety.

FIELD OF THE INVENTION

The invention relates to semi- and fully-automated methods and reagent compositions for assaying body fluid samples, particularly cerebrospinal fluid (CSF), for the detection and quantification of cellular components that may be found therein. The invention is relevant for clinical applications and provides assays that are efficient, accurate and reliable.

BACKGROUND OF THE INVENTION

Cerebrospinal fluid (CSF) is present between two meningeal membranes of the brain and is circulated over the cerebral hemispheres and spinal cord. The CSF acts as a protective cushion for the underlying central nervous tissue; other functions include collection of wastes, circulation of nutrients, and lubrication of the central nervous system.

The major clinical role of CSF analysis is in the diagnosis of bacterial meningitis, the differential diagnosis of viral and fungal meningitis, encephalitis, neurological disorders and the diagnosis of leukemias with CSF involvement. Other indications for CSF analysis include the monitoring of patients undergoing therapy for leukemias and lymphomas. The examination of CSF samples typically involves chemical and immunological studies, and, more particularly, microbiologic examination and hematological analysis to derive red blood cell count (RBC), white blood cell count (WBC) and WBC differential cell count. These results are correlated with clinical findings and radiographic studies to provide a clinical diagnosis.

Hematological analysis of CSF specimens is currently performed in the majority of hospital laboratories using manual cell counting and cell differentiation methods. These analyses are among the most laborious manual procedures in the clinical laboratory today. For instance, the analysis of one CSF specimen using current manual methods takes approximately 30-45 minutes. Currently, no automated method for CSF analysis is available on existing hematology platforms.

Automated cell counters or hematology analyzers, such as the ADVIA 120® analyzer (Bayer Corporation, Tarrytown, N.Y.), are typically designed to enumerate cells from samples of whole blood. The standard reagents used on such instruments are designed to compensate for, or take advantage of, various chemical effects of some of the major components of blood plasma, e.g., albumin, lipoprotein, and the like (see, for example, U.S. Pat. Nos. 3,741,875 and 4,412,004). Also, automated analyzers/cell counters typically count from about 2,000 to 50,000 cells in a single blood-dilution per analytical cycle. In addition, the presence of as few as 5 to 10 non-cellular particles (or 5 to 10 cells carried over from a previous cycle, i.e., carryover) which overlap the regions occupied by countable cells, causes only a very small loss of accuracy and/or precision in whole blood sample analysis. Further, instruments such as the ADVIA 120® are typically designed to accept a fixed-sized aliquot of whole blood which is automatically diluted to provide the required cell concentration for a fixed counting period.

Body fluids other than whole blood, for example, cerebrospinal fluid, normally contain no red cells or platelets, little or no dissolved protein and as little as 0.01% of the typical white blood cell count of whole blood. Therefore, if the same automated instruments that handle whole blood cell analyses are also used to determine the cell counts of such other non-blood body fluids, it is required that reagents and dilutions be designed to compensate for the typically nearly acellular conditions of such samples. Moreover, unlike whole blood cell analysis, if the analytical cycle of the instrument handles a volume of body fluid sample that contains only 5 to 10 authentic cells, the interference of non-cellular particles and carryover, referred to above, constitutes a problem in the analysis of such non-blood body fluids that contain very few cells.

Because of the low concentration of cells in samples of non-blood aliquots of body fluids such as CSF, the dilution of sample must be greatly reduced to provide useful precision for the same fixed counting period. Further, rare samples such as CSF are considered to be in a special category compared with whole blood samples. For example, body fluid samples, e.g., CSF, typically arrive in the laboratory infrequently and/or randomly; it is not usually convenient to interrupt the work-flow of the automated analyzer on whole blood samples to accommodate the analysis of the infrequent or random non-blood samples. As it happens, these types of samples are commonly analyzed immediately as "STAT" samples, but they may also be set aside to accumulate for later analysis and more efficient batch-processing. However, such untreated body fluid samples are usually less stable than are typical anti-coagulated whole blood samples, which can often be analyzed with accuracy even after 24 hours of storage at 2-6° C.

It is therefore desirable to be able to mix such non-whole blood body fluid samples with a reagent that fixes the cells in a state that safely permits their later accurate analysis, even after storage for up to 24 or more hours. In addition, for such special procedures involving non-blood body fluid samples, it is usually necessary to develop control materials, which are stable for at least a few months, and which can be used to confirm system gains, when necessary, so that the accuracy of the counts obtained using body fluid samples is assured. The present invention is designed to overcome and address these problems and needs.

In addition, the present invention offers automated methods and procedures, i.e., semi- and fully-automated methods and procedures, for analyzing body fluid samples, such as CSF, and advantageously provides the skilled practitioner with an efficient, reliable and less time-consuming assay for analyzing non-blood samples.

SUMMARY OF THE INVENTION

The present invention provides a newly developed assay (method) for the analysis of body fluid samples, particularly, cerebrospinal fluid (CSF) samples, which utilizes the direct cytometry feature of an automated cell counter or analyzer to provide and report values and parameters of red and white blood cells detected in the body fluid sample, e.g., a CSF sample. The method is semi-automated or fully-automated and is preferably performed on an automated hematology analyzer or flow cytometer, such as the ADVIA 120® hematology analyzer (Bayer Corporation, Tarrytown, N.Y.). The method is performed in conjunction with a reagent that spheres and fixes in suspension all of the cells in the sample. Further, in conjunction with gating software, the analysis and reporting of red blood cell count (RBC), white blood cell-count (WBC) and WBC differential values in a CSF sample undergoing analysis are achieved.

It is an aspect of the present invention to provide a semi- or fully-automated method to detect blood cell components of CSF in a rapid and reliable assay. Such blood cell components are typically in very low concentrations in CSF, thereby making them difficult to detect in a reliable way using conventional methods. According to the present invention, white blood cells, red blood cells, and WBC differential values can be determined and quantified as a result of the analysis of CSF in the automated hematology analyzer.

It is another aspect of the present invention to provide an aqueous reagent (reagent composition) for admixing with non-blood body fluid samples to be analyzed on an automated analyzer. In accordance with the invention, the body fluid samples include, for example, CSF, pulmonary or bronchial lavage fluid, synovial fluid, peritoneal fluid, and the like, as further described herein. The formulation of the reagent composition is particularly suitable for use in a semi-automated analysis method according to this invention.

Another aspect of the present invention provides a method for fixing and sphering cells in a body fluid sample, or aliquot thereof, so that the cells remain in suspension and maintain their volumes and contents for extended periods of time. In accordance with the method, an aliquot of a body fluid is mixed with an aliquot of an aqueous reagent composition comprising, in admixture, a solution of at least one aldehyde, at least one surface-active agent and cyclodextrin. In a preferred reagent composition according to this invention, the aldehydes are glutaraldehyde, formaldehyde, or a combination of glutaraldehyde and formaldehyde; the surface active agent is a zwitterionic detergent; and the cyclodextrin is a hydroxypropyl-β-cyclodextrin.

It is a further aspect of the present invention to provide a control material for flow cytometric analysis of the cells in body fluids, in which the control material comprises a mixture of cells of a body fluid to be analyzed and the above-described aqueous reagent composition according to the invention.

Yet another aspect of the present invention provides a control material for flow cytometric analysis of the cells in body fluids comprising cells after fixation and sphering in a mixture as described herein, wherein the cells are re-suspended in a different stabilized aqueous solution.

It is another aspect of the present invention to provide an automated direct cytometry analyzer configured with a mode of operation and associated types of performance cycles as described herein to achieve the analysis method for non-whole blood body fluid samples, e.g., CSF, according to the present invention.

Further aspects, features and advantages of the present invention will be better appreciated upon a reading of the detailed description of the invention when considered in connection with the accompanying figures/drawings.

BRIEF DESCRIPTION OF THE FIGURES

FIGS. 1A and 1B show Direct Cytometry cytograms of the PRP sample diluted 1:20 with phosphate buffered saline. White blood cells (LYMPHs, MONOs, NEUTs, platelets and EOS) form distinct clusters that are well separated from each other. Because red blood cells (RBCs) are not sphered, they do not form a distinct cluster and thus partly overlay the lymphocyte population. FIGS. 1C and 1D show CSF Direct Cytometry cytograms of the same PRP sample as in FIGS. 1A and 1B diluted 1:20 with the reagent composition of the present invention to fix and sphere the cells. The position of the fixed and sphered white cells has shifted as compared with FIG. 1A, and form more distinct cell clusters. In contrast to FIG. 1A, the fixed and sphered red blood cells seen in FIG. 1C now form a distinct cluster and do not overlay the lymphocytes. In contrast with FIG. 1B, eosinophils in FIG. 1D are seen to separate from the clearly formed neutrophil population.

FIG. 11A: analysis of a normal, nearly acellular CSF sample; FIG. 11C: analysis of a sample with low WBC counts; FIG. 11E: analysis of a sample containing WBC at a level of approximately 20 WBC; and FIG. 11G: analysis of a sample at the level of approximately 100 WBC/IL. The Tables below the cytograms of FIGS. 11A, 11C, 11E, and 11G, (i.e., in FIGS. 11B, 11D, 11F and 11H, respectively, present the CSF assay results obtained using the ADVIA 120® automated analyzer instrument and the reference manual results.

DETAILED DESCRIPTION OF THE INVENTION

Figure 1A:
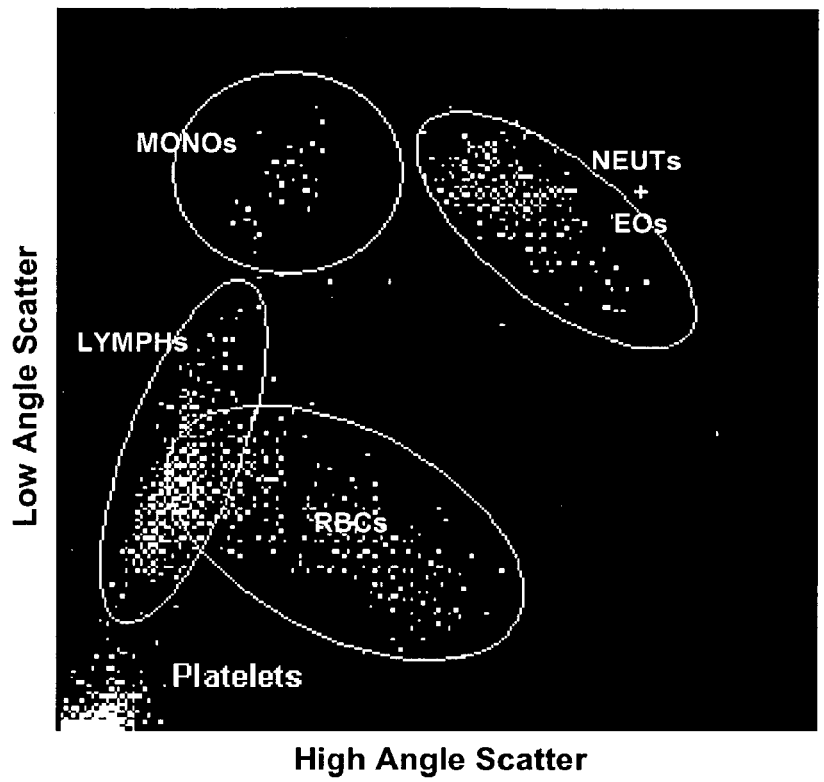
FIGS. 1A-1D depict cytograms of platelet-rich plasma (PRP) examined on an automated hematology analyzer (i.e., the Bayer ADVIA 120® automated analyzer, Bayer Corporation, Tarrytown, N.Y.).
Figure 1B:
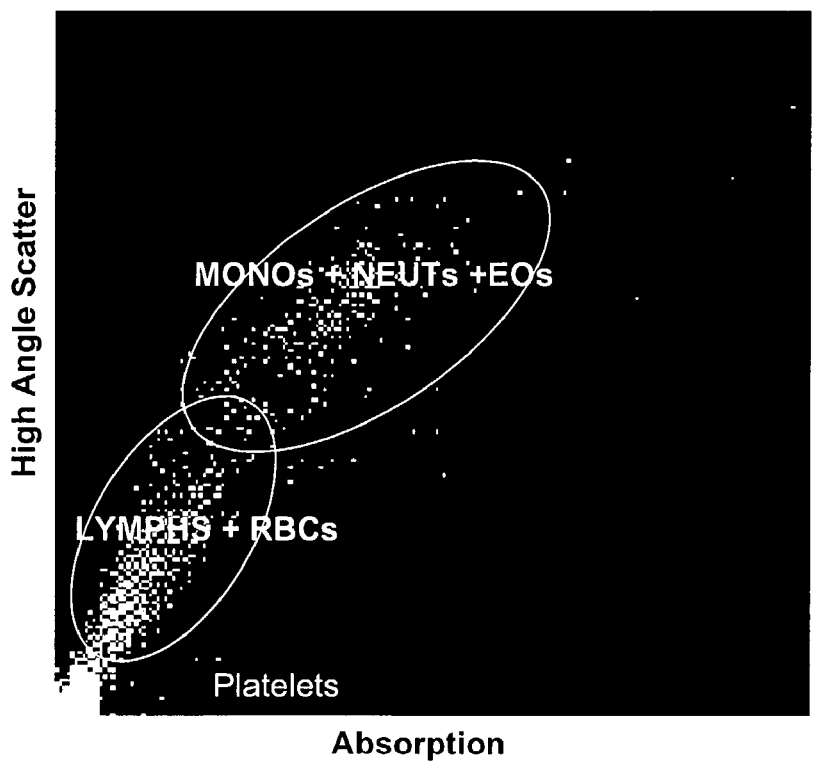

The present invention provides accurate and sensitive semi- and fully-automated assays and methods for the analysis of body fluid samples, such as CSF samples. An advantage of the method of this invention is the development and use of a direct cytometry sampling feature of an automated hematology analyzer or cell counter in conjunction with a reagent that spheres and fixes all cells that may be present in the sample, without cell lysis. The assay/method enables the analysis of typically low-volume, nearly acellular body fluid samples accurately, reliably and with sensitivity.

The analysis of CSF and other non-blood body fluids makes use of gating software used in the method, particularly when performed on a hematology analyzer such as the ADVIA 120® direct cytometry automated instrument (Bayer Corporation, Tarrytown, N.Y.). Newly developed hydraulic cycles performed on the analyzer permit the use of a small sample volume for analysis and maintain the degree of cleanliness needed for this assay.

The new sphering and fixing reagent used in the analysis preserves the prepared samples, thus extending the length of time post-draw that samples can be analyzed with accuracy. This allows body fluid samples, e.g., CSF samples, to be run in batch mode, if desired, or stored for up to a week at 4° C. for future analysis. Prepared CSF samples can be stored at room temperature (e.g., 18-30° C.) for several hours. Accordingly, the method and reagent of the present invention allow body fluid samples, such as CSF samples, to behave as well as, or even better than, blood samples in terms of their stability over time, until and during automated cytometry analysis.

Previously developed reagents for sphering blood cells include zwitterionic surfactants to isovolumetrically sphere both red blood cells and white blood cells (see, e.g., U.S. Pat. Nos. 4,412,004, 4,575,490, 5,045,472, 5,350,695, 5,360,739, 5,411,897, 5,438,003 and 5,633,167). When a zwitterionic surfactant (surface active agent) such as tetradecyl-N,N-dimethylammonio propane sulfonate (TDAPS) is used at a concentration of 8.3 mg/L in an otherwise isotonic physiological solution to dilute platelet-rich plasma (PRP), 1:20, and the cells are examined by Direct Cytometry in the RBC mode on an ADVIA 120® automated analyzer, a cytogram like that of FIG. 1C is obtained.

With further regard to PRP, it is well known that when a freshly mixed anti-coagulated sample of normal blood is set aside, the biconcave red cells begin to form stacks of cells, like stacks of coins. These begin to sediment at speeds much greater than the settling rate of individual cells (red cells, white cells, or platelets). After a period of from about 30 minutes to about 120 minutes (depending upon the particular blood sample), the blood will have separated into two zones: a dark red-colored lower zone of packed red cells, and a yellowish-pink upper layer of white cells and platelets suspended in plasma, with also from about 1 to 2 unsedimented red cells per white cell. If sedimentation is permitted to extend too long, many of the white cells also descend to the top of the red cell layer to form what is referred to as the Buffy Coat. The upper layer is usually referred to as the Platelet Rich Plasma (PRP).

Figure 1C:
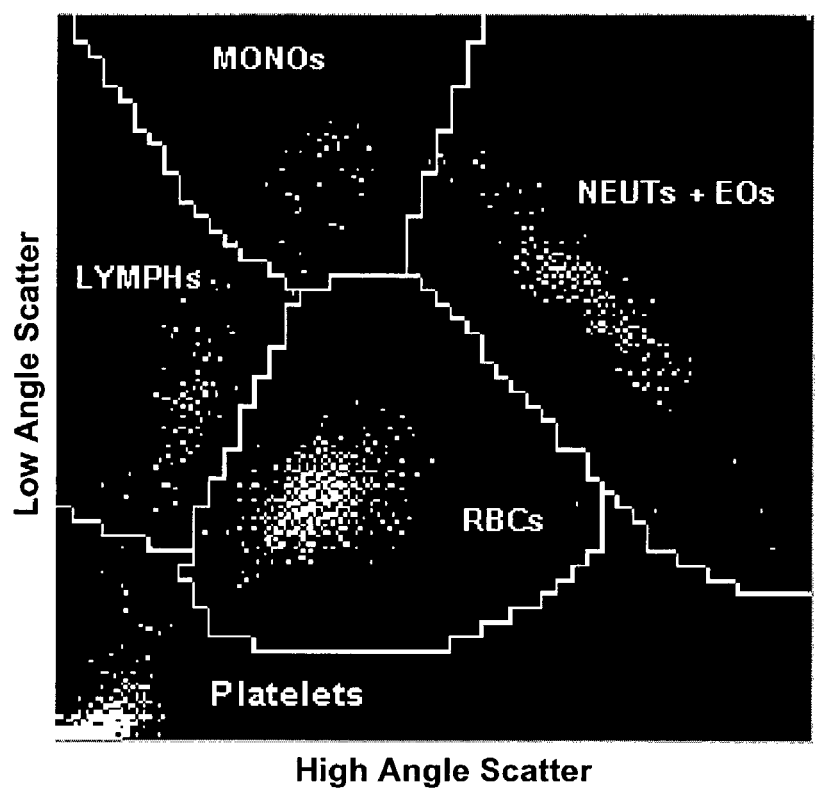
Figure 1D:
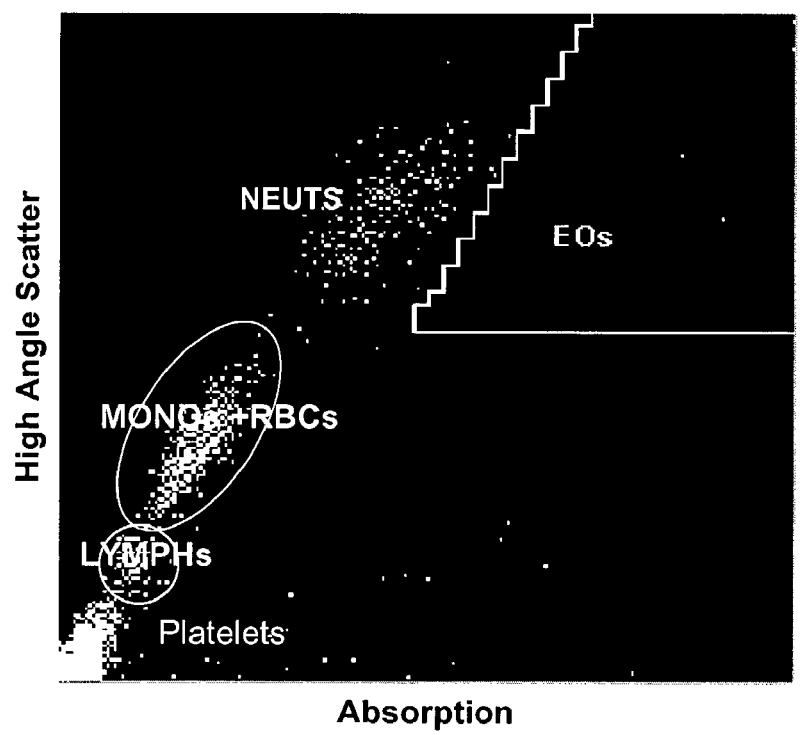
Figure 1E:
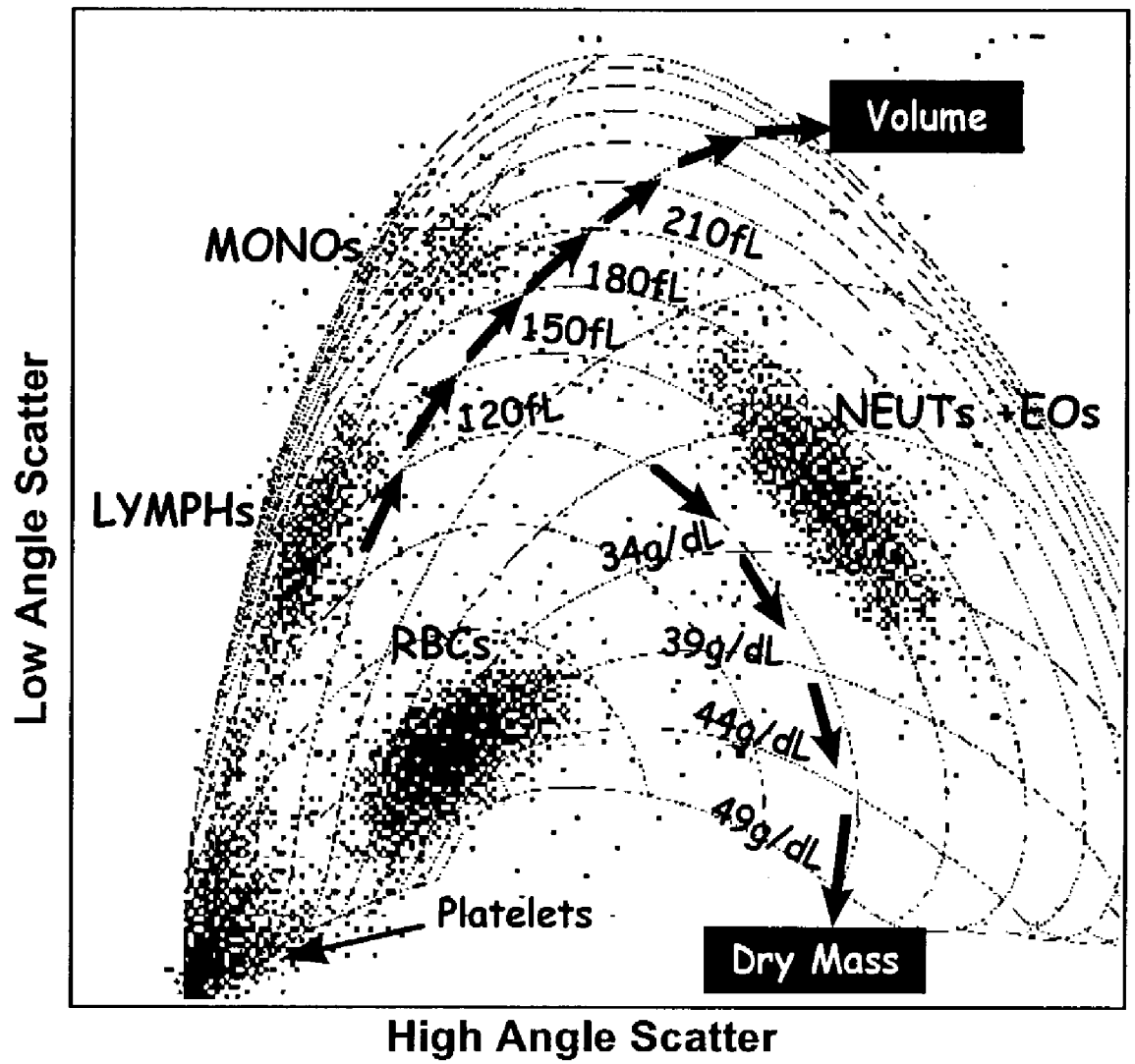
FIG. 1E shows the cytogram of a fixed and sphered PRP sample with an overlaid Mie-Map where one set of coordinates represents cell volume, and the other (almost orthogonal) set represents refractive index (which is proportional to dry-mass concentration). Volume varies from 30-410 fL on the map and is shown in increments of 30 fL. Dry Mass varies from 0-49 g/dL and is shown in increments of 5 g/dL. Neutrophils, for example, have an average volume of between 150-180 fL and an average Dry Mass of between 29-34 g/dL.
Figure 2:
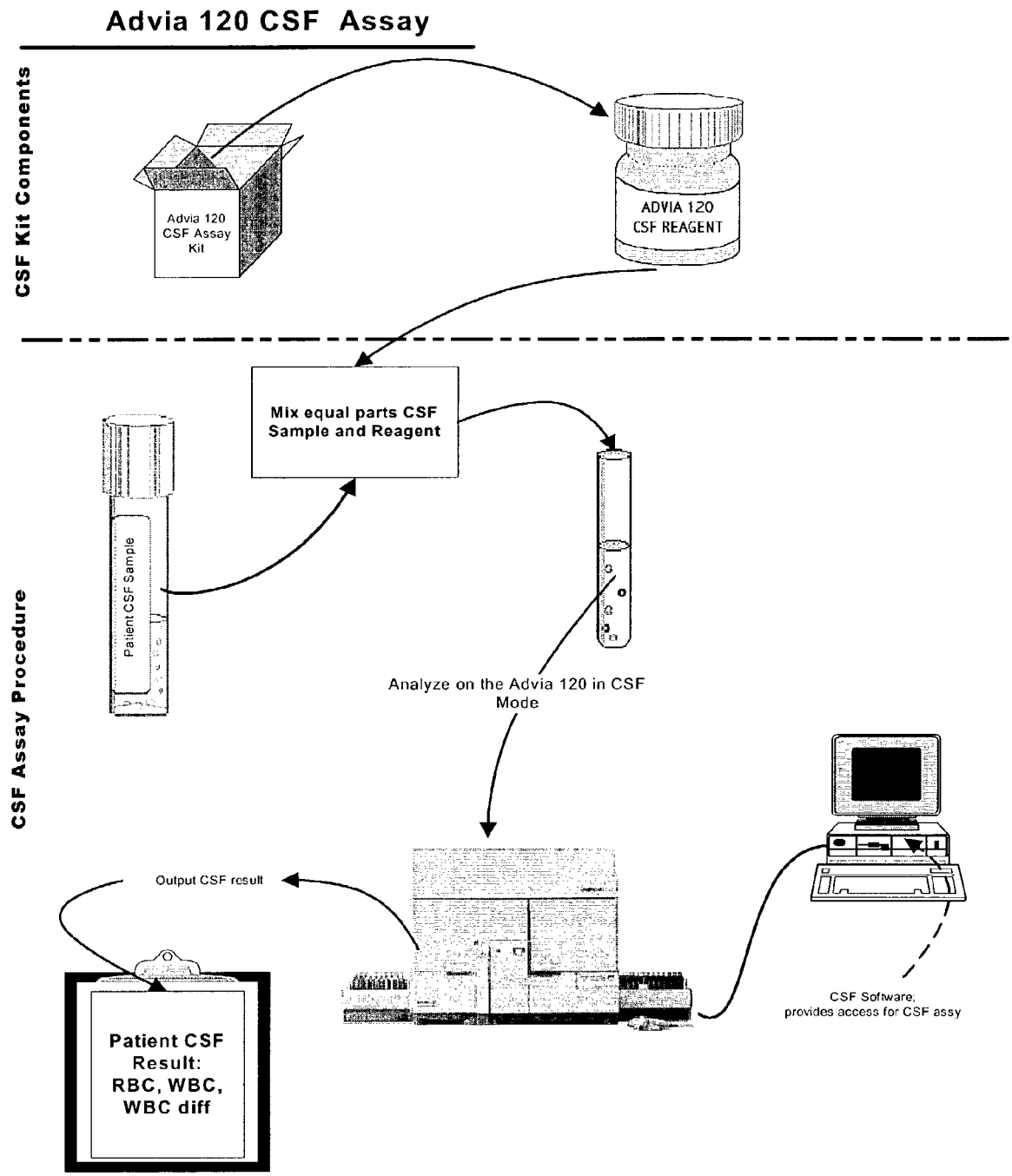
FIG. 2 illustrates a schematic flowchart of the semi-automated CSF or other body fluid assay according to the present invention, as performed using the exemplified ADVIA 120® Hematology Analyzer (Bayer Corporation, Tarrytown, N.Y.).

The clusters of points representing lymphocytes, monocytes, neutrophils, eosinophils, platelets and red blood cells are individually labeled on the cytograms of FIGS. 1A, 1C and 1E. The locations of these cells in these representative cytograms serve as a useful frame of reference for further discussion of the present invention.

Accordingly, it is desirable that a body fluid, such as CSF, which normally has few cells, be processed to produce a cytogram with almost the same locations for each of the cell types as those shown in FIG. 1C. This is because the numbers of cells in each cluster of cells are able to be precisely counted with appropriate thresholding algorithms using automated cell counters that are typically employed for blood analysis. In addition, the position of each sphered cell records two valuable parameters for characterizing the sphered cell: namely, its precise volume and its dry-mass concentration, (FIG. 1E), (see, e.g., Tycko, D. H. et al., 1983, "Cell by cell determination of and hemoglobin of isovolumetrically-sphered human red blood cells: A precision cytophotometric surrogate for red cell 'morphology'", *Proc. Clinical Application of Flow*, Sea Island, Ga.; Tycko, D. H. et al., 1985, "Flow-cytometric light scattering measurements of red blood cell volume and hemoglobin concentration", *Appl. Optics*, 24, 1355-1365; and U.S. Pat. Nos. 4,735,504 and 6,025,201).

It is well known that aqueous solutions of aldehydes, such as formaldehyde and glutaraldehyde are useful to fix cells, both for typical histological purposes as well as for flow-cytometric analysis (see, e.g., U.S. Pat. Nos. 3,741,875, 4,412,004 and 4,475,490). Glutaraldehyde is usually more effective at lower concentrations than is formaldehyde, and fixes the cells more rapidly. On the other hand, the fixation must not be so rapid as to fix the shape of the non-spherical cells before the sphering agent can do its job. Therefore, the choice of ratios of aldehyde to sphering agent concentrations, as well as absolute concentrations of reagents, is relatively critical in a fixation process and reagent for samples that are to be analyzed.

Further, the ratio of sphering agent to protein in the final reagent-plus-sample mixture can also be critical, because adequate concentration of protein is needed to "buffer" the surfactant. However, it has been indicated that with the use of zwitterionic surfactants, the problem is less severe for red cells. (see, e.g., U.S. Pat. No. 5,633,167). For example, when various combinations of glutaraldehyde and TDAPS were mixed with PRP diluted 1:20 with isotonic saline at neutral pH, it was found that the concentration of TDAPS that was just sufficient to perfectly sphere the red cells resulted in the positions of some of the white cells usually falling to the left of, and below, the positions in the reference cytogram of FIG. 1C. Based on the position of the white cells in the FIG. 1C cytogram, it was determined, with reference to the Mie-map, that these cells had changed volume, leaked solutes and lost dry mass. However, if the PRP was diluted with cell-free plasma instead of isotonic saline, using the same concentrations of TDAPS and glutaraldehyde, the cells were returned to their "correct" locations in the cytogram. Thus, although a zwitterionic surfactant is more "forgiving" of damage to red cell membranes in the presence of large variations in protein concentration, this appears to be less so for white cells in the blood sample.

For the purposes of formulating a reagent composition for body fluid sample dilution and/or mixture, it is not convenient to prepare reagents containing plasma or proteins as ingredients or components, especially in the presence of aldehydes, because aldehydes typically react with proteins and cross-link them, thereby changing their solubility, stability and buffering capacities. Thus, in accordance with the present invention for use with body fluid samples other than whole blood samples, a reagent composition was designed which comprises a relatively aldehyde-inert material to replace plasma protein, to act as a buffer for the surfactant, and to bind it in a reversible manner.

The materials used and newly discovered as suitable ingredients for inclusion in the reagent composition for admixing with non whole blood body fluids are cyclodextrins. Preferred are hydroxypropylated-β-cyclodextrins because of their greater water solubility. Unmodified alpha (α), beta (β) and gamma (γ) cyclodextrins are also suitable; however, it will be appreciated that the lower water solubilities of these latter types of cyclodextrins somewhat limit the formulations that can be used for preparation of concentrated stock solutions that contribute to convenience of manufacture.

Thus, one embodiment of the present invention provides an aqueous reagent composition particularly suited to mixing with body fluids, such as CSF, for analysis using an automated hematology analyzer instrument. In accordance with the present invention, the reagent is employed for fixing and sphering cells in an aliquot of body fluid so that the cells remain in suspension and maintain their volumes and contents for extended periods of time. The method involves mixing an aliquot of a body fluid with an aliquot of the aqueous reagent, i.e., reagent composition, comprising a solution of appropriate aldehydes, surface-active agent and cyclodextrin to form a reagent mixture, and analyzing the mixture, virtually one cell at a time, on an automated analyzer using. Direct Cytometry.

The aqueous reagent formulation of the present invention comprises at least one fixative, preferably, formaldehyde, glutaraldehyde, or a combination thereof. The formaldehyde content in the reagent is controlled by the addition of formalin, which is a 37-WT % solution of formaldehyde in water. In the CSF reagent, formaldehyde is present in an amount of from about 10 g/L to about 25 g/L; particularly from about 15 g/L to about 23 g/L; more particularly from about 17 g/L to about 23 g/L; most particularly, from about 17.03 g/L to about 23.05 g/L; preferably from about 18.0 g/L to about 21.0 g/L, and more preferably, from about 19.0 g/L to about 21.0 g/L.

The glutaraldehyde content in the reagent is controlled by the addition of glutaraldehyde as a 25-WT % solution or a 5-WT % solution. Glutaraldehyde is present in the CSF reagent in an amount of from about 1 g/L to about 5 g/L; particularly from about 2 g/L to about 3 g/L; more particularly, about 2.1 g/L to about 2.9 g/L; still more particularly, from about 2.3 g/L to about 2.8 g/L; preferably from about 2.25 g/L to about 2.75 g/L; and more preferably, from about 2.4 g/L to about 2.6 g/L. The formulation also comprises a cyclodextrin, preferably hydroxypropylated β-cyclodextrin, in an amount of from about 10 g/L to about 35 g/L; particularly from about 14 g/L to about 35 g/L; more particularly, about 14.1 g/L to about 35.2 g/L; preferably from about 15 g/L to about 21 g/L; more specifically from about 15.5-15.8 g/L to about 21-21.1 g/L; and more preferably from about 16.7 g/L to about 18.5 g/L. In addition, a surface active agent, i.e., a detergent or surfactant, comprises the reagent formulation in an amount of from about 1.5 g/L to about 3.0 g/L; preferably from about 1.8 g/L to about 2.5 g/L; more preferably from about 1.8 g/L to about 2.2 g/L; still more preferably, from about 1.9 g/L to about 2.1 g/L; and even more preferably, from about 1.88 g/L to about 2.12 g/L.

Suitable surface active agents, i.e., surfactants or detergents, that may be employed in the reagent of the invention include nonionic and zwitterionic surfactants. Several general classes of zwitterionic surfactants, or nonionic surfactants, may be used as sphering agents in the reagent composition of the present invention. The surfactant is present in the composition in an amount effective to substantially sphere any cells that may be present in the body fluid sample undergoing analysis.

Nonlimiting examples of suitable classes of zwitterionic surfactants include betaines, including carboxybetaines, sulfobetaines (also known as sultaines), amidobetaines and sulfoamidobetaines. Of particular interest for use in the reagent composition are the $C_8$-$C_{18}$, preferably $C_{10}$-$C_{18}$, alkyl betaines, sulfobetaines, amidobetaines, and amidobetaines, for example, those of the laurylamidopropylbetaine (LAB) type.

Nonlimiting examples of suitable zwitterionic surfactants in the betaine class include n-alkyldimethylammonio methane carboxylate (DAMC), n-alkyldimethylammonio ethane carboxylate (DAEC) and n-alkyldimethylammonio propane carboxylate (DAPC). Examples of the sulfobetaine class of zwitterionic surfactants include, but are not limited to, the n-alkylsultaines, or n-alkyl dimethylammonio alkyl sulfonates, such as n-alkyl dimethylammonio methane sulfonate (DAMS), n-alkyl dimethylammonio ethane sulfonate (DAES), n-alkyl dimethylammonio propane sulfonate (DAPS) and n-alkyl dimethylammonio butane sulfonate (DABS). In the "DAPS" surfactant series, TDAPS, wherein "T" is n-tetradecyl; DDAPS, wherein "D" is dodecyl, is especially suitable and is preferred in the present invention.

The amidobetaines include, but are not limited to, n-alkylamidomethane dimethylammonio methane carboxylate or n-alkylamido methane dimethylammonio ethane carboxylate. A preferred amidobetaine is laurylamidopropylbetaine (LAB). Also suitable are the analogous amidobetaine sulfonates, such as n-alkylamidomethane dimethylammonio methane sulfonate, n-alkylamidoethane dimethylammonio ethane sulfonate and n-alkylamidopropane dimethylammonio propane sulfonate. In addition, amidobetaines which have coconut oil as their fatty acid source, e.g., cocoamidopropylbetaine (CAPB) and cocoamidosulfobetaine (CASB), may be considered for use. Further descriptions of betaines, sulfobetaines, amidobetaines and amidosulfobetaines may be found in the pertinent literature, for example, S. Takano et al., 1977, *J. Amer. Oil Chem. Soc.*, 54:139-143 and 484-486; Z. El Rossi, C. Horvath, 1982, *Chromatographia*, 15:75-82; Kaminski and Linfield, 1979, *J. Amer. Oil Chem. Soc.*, 56:771-773.

Other zwitterionic surfactants suitable for use include 3-[(3-cholamidopropyl)dimethylammonio]-1-propanesulfonate (CHAPS) and 3-[(3-cholamidopropyl)dimethylammonio]-2-hydroxy-1-propanesulfonate (CHAPSO).

Nonionic surfactants that are suitable for use in the present invention generally include alkylglycosides. Preferred nonionic surfactants include n-dodecyl-β-D-maltoside, n-tetradecyl-β-D-maltoside and n-tetradecyl-β-D-glucoside.

Buffering agents are also typically included in the formulation of the reagent composition of the present invention to maintain the pH in the range of about pH 4.0 to pH 7.0, preferably, pH 4.5 to pH 6.5; and more preferably pH 5.0 to pH 6.4; and even more preferably, about pH 5.0 to 5.6. At the top of the pH range, the shelf-life of the glutaraldehyde component of the reagent is generally reduced; at the bottom of the pH range, the glutaraldehyde can out-compete the formaldehyde, leading to early onset of cell and protein clumping. Non-limiting examples of buffering agents include salts, such as $Na_2HPO_4$ and/or $NaH_2PO_4$, citric acid and its salts, succinic acid and its salts, and EDTA and its salts, e.g., $K_3$ EDTA, etc., in an amount of about 40 mMol to about 60 mMol, more preferably, from about 48 mMol to about 52 mMol.

Citric acid has three pKa's, namely, 3.13, 4.67, and 6.40; therefore, it is a good buffer for the purpose of the present invention, particularly in a pH range of between about pH 4.8 and about pH 6.4. Above 6.4, phosphate buffer would preferably be used. The reagent composition may also contain a chelating agent, for example, ethylenediaminetetraacetic acid (EDTA), or salts thereof, (e.g., $K_3$ EDTA), to maintain reagent stability.

Especially preferred in the reagent composition according to the invention is a combination of glutaraldehyde and formaldehyde (formaldehyde quickly fills the cell-surface sites that otherwise lead to delayed glutaraldehyde-induced cell-to-cell and plasma protein cross-linking, which then leads to cell clumping and/or protein precipitation); with hydroxypropyl-β-cyclodextrin, and with the zwitterionic surfactant TDAPS.

An exemplary and nonlimiting final formulation of a concentrated stock solution of the above-described reagent according to this invention, for ultimate dilution to a working solution as described below, contains aqueous (20-67.6 g/L) formalin (7.4-25 g/L formaldehyde), 1-6 g/L glutaraldehyde, 15-42 g/L hydroxypropyl-1-cyclodextrin (Cerestar 82004), and 2-6 g/L TDAPS adjusted to pH 5-8 with a buffer salt such as sodium citrate or $Na_2HPO_4$. A list of the preferred components of the reagent composition of the present invention and their preferred amounts as used in the semi-automated assay embodiment of the invention is shown in Table 1. The preferred pH range for the CSF reagent presented in Table 1 is about 5.3-5.5. This reagent composition shows stability both for use in the method and for long-term storage, e.g., at least a year. It is to be understood that the preferred reagents and amounts are provided for example and guidance and are not intended to be limiting.

TABLE 1

Preferred embodiment of the CSF Reagent Components

| Component | Amount (g/L) |
|---|---|
| Formalin (0.37 solution) | 54.15 |
| Glutaraldehyde (0.50 solution) | 5.53 |
| N-tetradecyl-N,N-dimethyl-3-ammonio-1-propanesulfonate (TDAPS) | 2.00 |
| β-hydroxypropyl cyclodextrin (Cavitron) | 17.6 |
| Citric Acid Monohydrate (50 mmol/L) | 10.5 |
| Disodium Ethylenediaminetetraacetic Acid ($Na_2$EDTA dihydrate) | 0.74 |

Typically, a working solution is made by diluting the stock solution, e.g., 1:5 to 1:20, with isotonic (e.g., 290 milliOsmolal, mOsmol/Kg; mOsm) saline or other physiologic solution. For some purposes, tonicity as low as 200, and as high as 400 mOsm saline solutions can be used. The working solution is preferably formulated at a working tonicity of about 1060 mOsm to about 1080 mOsm and is usually mixed with a body fluid sample such as CSF, at a dilution of 1:1. It is to be noted that most of the tonicity of the working solution is due to the formaldehyde which readily and rapidly passes through cell membranes and thus contributes little to the otherwise severe osmotic shrinking to be expected from a 1000 mOsm solution of non-permeating solute. In fact, after a 1:1 dilution, the osmotic effect of the working solution is equivalent to about a 360 mOsm salt solution.

Figure 3A:
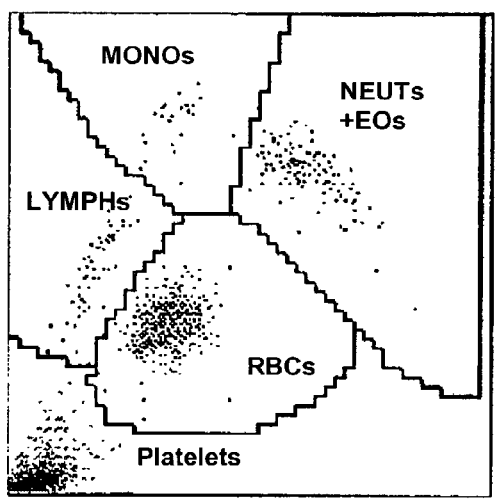
FIGS. 3A-3C illustrate the effects of varying reagent osmolalities on a sample. (Table 2). The same PRP sample is shown using reagents with a target osmolality of 1070 mOsm (FIG. 3A), a high osmolality of 1140 mOsm (FIG. 3B) and a low osmolality 1024 mOsm (FIG. 3C). It is to be noted that after a 1:1 dilution, the foregoing yield solutions that are osmotically equivalent to solutions of about 360 mOsm, 430 mOsm and 314 mOsm, respectively, of non-permeating solutes. Although white cell populations shift clockwise with increasing osmolality, they still fall within appropriate gating areas in the cytogram and can be correctly analyzed. This demonstrates that the reagent composition according to the present invention can be formulated at a range of osmolalities.
Figure 3B:
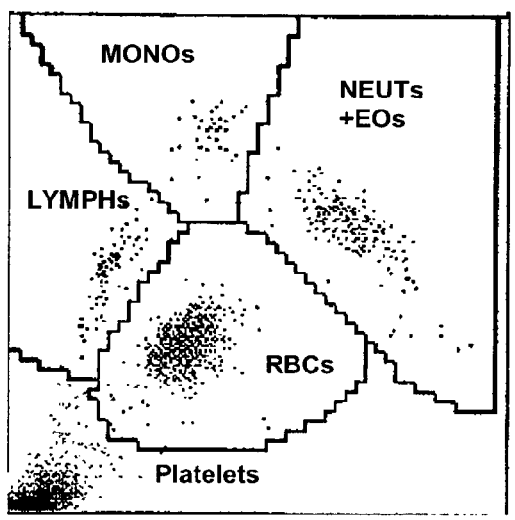
Figure 3C:
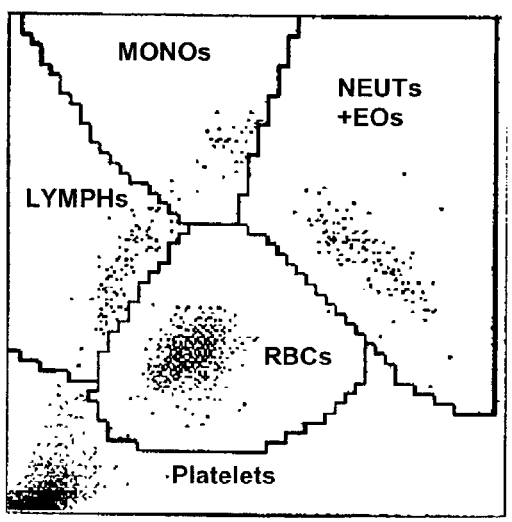

Table 2 and FIGS. 3A-3C show the results of the CSF assay performed using reagents having several different osmolalities. The white blood cell populations fall within appropriate gating areas in the cytograms (FIGS. 3A-3C) and can be correctly analyzed, despite a shift clockwise with increasing osmolality. Accordingly, the reagent according to the present invention is suitably formulated at a range of osmolalities, as shown herein.

TABLE 2

| Parameter | Low Osmolality 1024 mOsm | Target Osmolality 1070 mOsm | High Osmolality 1140 mOsm |
|---|---|---|---|
| WBC | 95 | 91 | 99 |
| RBC | 175 | 174 | 177 |
| % Lymphocytes | 29 | 26 | 27 |
| % Monocytes | 12 | 12 | 11 |
| % Neutrophils | 58 | 61 | 61 |
| % Eosinophils | 1 | 1 | 1 |

As an example, in a preferred embodiment for the CSF analysis method, an equal volume of CSF sample is mixed with an equal volume of CSF reagent and run on an automated instrument, such as the Bayer ADVIA 120® automated analyzer. The volume of CSF sample that can be analyzed by the instrument is 3.7 times greater than the maximum volume (e.g., 1 μL) that currently can be analyzed by microscopic examination of CSF in a hemacytometer. As a result, there is a square root of 3.7 (i.e., $\sqrt{3.7}$) improvement in counting precision. The present method is thus advantageous due to its ability to quickly, accurately, reliably and efficiently analyze samples like CSF, which are typically acellular, or close to acellular.

Another aspect of the present invention encompasses the analysis of samples of bodily fluids in addition to and other than cerebrospinal fluid (CSF), for example, pleural fluid samples, pulmonary or bronchial lavage fluid samples, synovial fluid samples, peritoneal fluid samples, bone marrow aspirate samples, ascites fluid samples, sputum samples, saliva samples, lymph, tears, serum, plasma, semen, urine, or bladder wash samples, and the like. Such samples frequently, although not necessarily, contain very few cells. When the concentration of cells is substantially higher than in CSF, a greater than 1:1 dilution with sphering/fixing reagent is used. Accordingly, the sensitivity of the present method is well suited for the analysis of cells in a variety of different body fluid samples. Such body fluid samples can also be mixed with the reagent composition of the invention to prepare a more stable reagent mixture having at least an 8 hour stability at room temperature, and a greater than 24 hour stability at 4° C.

In a particular yet nonlimiting embodiment, the present invention encompasses the analysis of CSF samples on the ADVIA 120® hematology analyzer. With appropriate system/software modifications, including changes to timing cycles and analysis algorithms, other applications of this invention may include the monitoring of fresh frozen plasma units in blood banks for the presence of residual RBCs, WBCs and platelets. Typical acceptable cell levels for quality control of these units are: less than $1\text{-}6\times10^3$ RBC/µL, less than 100 WBC/µL and less than $20\times10^3$ PLT/µL, respectively.

As encompassed by the present invention and as described herein, a reagent composition has been developed, called the ADVIA 120® CSF reagent herein, to prepare CSF samples for analysis on the ADVIA 120® analyzer. It is to be understood that the reagent and method as described for CSF samples are also suitable for the analysis of other body fluid samples, as contemplated by the present invention and set forth above. As used herein, the terms "CSF assay" or "CSF reagent" is thus meant to include assays and reagents for other typically nearly acellular body fluids, in addition to CSF, as denoted elsewhere herein.

In one embodiment, the ADVIA 120® CSF method comprises an offline preparation where equal volumes of the fluid sample, e.g., the spinal fluid sample, and the sphering/fixing reagent composition, are combined and mixed to form a reagent/sample mixture. That is, the user manually processes the sample for analysis by mixing equal amounts of sample fluid (CSF sample) and CSF reagent and aspirates the mixture into the ADVIA 120® automated instrument.

The prepared and mixed sample comprising the reagent mixture containing an aliquot of a body fluid sample, (CSF, for example), and the CSF reagent composition is present in a glass or plastic tube prior to aspiration into the ADVIA 120® analyzer. One sample aspiration is sufficient to yield reportable white cell and red cell parameters (e.g., WBC, RBC, and a 4-part WBC Differential, i.e., the numbers and percentages of lymphocytes, monocytes, neutrophils and eosinophils) for the sample undergoing analysis.

Most cell-containing CSF samples include small numbers of white blood cells, with even smaller numbers of red blood cells and platelets. These factors make it possible to simultaneously enumerate and classify all of the cell types in a CSF sample more easily than in whole blood samples. By contrast, whole blood samples contain large numbers of red cells, platelets, and white cells. The concentration of red cells is so high that the blood sample must be diluted substantially to achieve a proper count. Even under these conditions, the number of simultaneous occurrences ("coincidences") of two or more red cells in the sensing zone of a typical hematology analyzer is 4%-7% of the total number of events counted.

In the automated detection system as described herein and below, red cells, platelets, and white cells occupy distinct signal detection regions, or clusters. However, red-cell coincidence signals occupy the same signal detection region as neutrophils, eosinophils, and in some cases, monocytes. Since in whole blood, the ratio of red cells to white cells is typically 500 to 1, red cell coincidence signals mask these white cell signals so that they may not be properly classified. Therefore, it is necessary to analyze white cells separately from red cells and platelets in whole blood samples. This is usually achieved by first lysing the red cells and then analyzing the remaining platelets and white cells.

In contrast, the small number and relative concentration of red cells and platelets to white cells in CSF, or other non-blood body fluid samples, usually make it possible to enumerate and classify all of these sample components within a single measurement channel, in a single analytical cycle. The low concentration of red cells in such non whole blood samples results in little or no red cell coincidence, so that neutrophils, eosinophils, and monocytes are not masked.

Based on the foregoing, a suitable method for body fluid cellular analysis, e.g., CSF cellular analysis, involves the single-file passage (i.e., virtually one cell at a time) of the cells in a body fluid sample through the sensing zone (flow cell) of an optical flow cytometer. As each cell interrupts a beam of monochromatic light focused onto the flow cell, it scatters the light in a manner that is characteristic of the cell's size and refractive index. Three suitably placed detectors produce signals in scatter/scatter space and scatter/absorption space that form distinct clusters of red cells, lymphocytes+basophils, monocytes, neutrophils, and eosinophils, as well as platelets.

Current automated analyzers and flow cytometric analyzer systems that can be used, or adapted for use, in practicing the method of the present invention, include the BAYER H*™ series of automated hematology analyzers, e.g., the BAYER H*3™ analyzer; and the ADVIA 120® analyzer, commercially available from Bayer Corporation, Tarrytown, N.Y. Such analyzer instruments are suitable for use with scatter/scatter and scatter/absorption systems for cell detection and qualitative and quantitative analysis of cell parameters. Non-limiting descriptions of such analyzers are found in U.S. Pat. No. 5,817,519 to D. Zelmanovic et al; U.S. Pat. Nos. 5,438,003 and 5,350,659 to G. Colella et al., and U.S. Pat. No. 4,735,504 to D. Tycko, the contents of which are hereby incorporated by reference in their entirety. It will be appreciated that other hematology analyzer systems having appropriate hardware and system components may be used, or adapted for use, in accordance with the present invention.

The low sample dilution according to the invention enables a larger number of cells to be counted automatically versus a manual determination, thus providing more accurate and precise results. Performance specifications are based on normal and abnormal CSF samples run on an ADVIA 120® automated system configured with CSF software. The reagent mixture comprising the sample is aspirated through the direct cytometry hydraulic pathway of the ADVIA 120® hematology analyzer using analytical and utility cycles for CSF analysis. The CSF analytical cycle permits the aspiration of a minimal volume of the prepared sample. The utility cycles (refresh and wash) are innovative hydraulic cycles that maintain the cleanliness of the fluidic pathway. Via its computer component, the ADVIA 120® analyzer typically calculates RBC and WBC absolute counts, and WBC differential parameter values, from the aspirated sample component of the reagent mixture. Optionally, the volume and dry-mass concentration of each cell and the average values and ratios of these parameters can also be recorded.

The volume of CSF sample analyzed by the instrument during the assay is 3.7 times greater than the volume typically analyzed by microscopic examination of CSF in a hemacytometer. Thus, the present method provides a $\sqrt{3.7}$-fold improvement in counting precision.

In another embodiment, a fully-automated method is contemplated by the present invention. The fully automated method comprises automated mixing of an aliquot of the body fluid sample with the reagent composition in the instrument subsequent to aspiration and then performance of the assay by the automated analyzer. Such a fully automated assay increases efficiency by eliminating the need for manual manipulations by the operator. However, it is to be appreciated that if samples are to be stored for longer than about 4 hours, the semi-automated method is preferred, because it prevents sample deterioration by cell fixation.

The CSF reagent of the present invention comprises reagent compounds that sphere and fix any cells within the sample. To verify proper reagent performance, quality control (QC) products are preferably assayed prior to the assay of each sample or each batch of samples (e.g., CSF samples). Preferably, the CSF assay is only accessible to a user who has access to the CSF software. Different avenues of selective accessibility can include, for example, a reagent barcode, wizard key, or smart card.

In the particular embodiments in which the ADVIA 120® instrument performs the semi- or fully-automated CSF assay, the automated analyzer performs several cycles associated with sample analysis as described herein. For direct cytometry analysis, preferably, semi-automated analysis according to the present invention, the introduction of a body fluid sample, e.g., a spinal fluid sample, for analysis by the system is accomplished by open tube aspiration. The operator immerses the aspiration probe into the prepared sample and triggers aspiration by depression of the aspirate pad on the front of the system. The CSF analytical cycle occurs in three stages: shuttle, count and cleaning.

During the shuttling phase, the vacuum shuttle chamber (VSC) vent and waste valves open almost simultaneously to purge any remaining fluids held in the shuttle chamber. Then the VSC vent port closes, the VSC sample inlet opens, and the RBC Direct Cytometry valve opens allowing the system vacuum to draw the sample up through the RBC direct cytometry lines. The sample passes rapidly through the Unified Fluidics Circuit (UFC) into the sample line of the RBC concentric flow module (CFM) and out of the CFM shuttle port to the shuttle chamber in the UFC. While the sample is being shuttled, a precise amount of sample is pulled into the sample pump as the plunger is driven down.

The counting phase begins as the RBC Sheath valve and Flow cell outlet valves open and the sample pump is driven up while the sheath pump is simultaneously pulled down. The effect is to pull the sample and sheath through the CFM and flow cell at a constant velocity. During the passage of the sample through the flow cell, the signals generated by cells in the sample are acquired. At the end of the sample counting, the RBC Sheath valve and Flow cell outlet close and the RBC Sheath Syringe Waste valve opens. The sheath syringe then pushes upward, sending the analyzed fluid to waste. The cleaning phase follows immediately, pushing rinse solution (e.g., universal rinse reagent solution, as described in U.S. Pat. No. 5,888,752) through the sample lines and drying them in preparation for the next sample.

In addition to the CSF analytical cycle, two other cycles have been developed for use with the automated CSF assay. The CSF refresh cycle has been designed to read the background count of the rinse in the flow cell to ensure system cleanliness prior to aspiration of the prepared sample. When requested by the operator, the CSF refresh cycle pushes rinse into all reaction chambers in the UFC block, and washes and dries the front end pathways (i.e., aspiration probe, sample shear valve and associated lines) of the analyzer. The system then aspirates the rinse through the flow cell using the same technique described in the counting phase of the CSF analytical cycle, thereby acquiring a count of the fluid passing through the flow cell.

The CSF wash cycle is designed to provide an additional cleaning cycle that specifically addresses the direct cytometry lines and valves. Upon initiation, the system opens the RBC Sheath line and both the RBC and Perox Direct Cytometry valves. As the cycle progresses, rinse is backflushed through the CFM sample line into the Perox chamber via the direct cytometry pathways. The Perox waste valves open to effectively pull the backflushed effluent to waste.

For fully-automated analysis, the raw CSF sample is directly aspirated into the ADVIA 120® sample probe and dilution with an equal volume of sphering/fixing reagent occurs internally.

CSF sample preparation for the semi-automated embodiment of the present invention involves manual dilution of the CSF sample with the CSF reagent of the invention. The cell density of the CSF sample, as reflected by the CSF sample appearance, determines the ratio of CSF sample to CSF reagent to be used. For example, samples containing a large number of red cells will appear pink to red, and samples containing a large number of white cells will appear whitish-opaque. Samples such as these require a pre-dilution prior to the 1:1 dilution with working solution, compared with a clear colorless sample containing relatively few cells, which does not require predilution. After a minimal incubation time of about 5 minutes, the prepared sample is analyzed on the ADVIA 120® analyzer in CSF mode. A CSF sample that is prepared for automated analysis, e.g., via a semi-automated method, is stable for about 5 minutes to about 4 hours at room temperature or 4° C.

In a preferred aspect, the ADVIA 120® analyzer is configured to run and analyze samples in the CSF assay as an integral part of the system. In general, the available WinMDI software package (The Scripps Research Institute, La Jolla, Calif.) is used to analyze flow cytometry data on the ADIVA 120® system so that CSF sample analysis can be performed. CSF samples are processed with the clinical ADVIA 120® software, in the CSF mode. CSF samples can be run singly or in batch mode from the Manual Open Tube (MOT) sampler. The physical characteristics of the CSF patient sample are entered as coded comments into the instrument. The Bayer ADVIA 120® instrument provides a new CSF Run Screen for the analysis of each new CSF sample. CSF samples have their own unique set of unit options, i.e., counts can be recorded in units of cells/µL or cells/L. Access to the computer contained CSF software can be provided, for example, by a smart card, wizard, barcode or a key.

The parameters measured by the CSF assay of the present invention are provided in Table 3.

TABLE 3

| | Reportable Parameters | |
|---|---|---|
| Parameter | Units | Analytical limits |
| White Blood Cells (WBC) | Cells/µL | On samples 0-5000 cells/µL |
| Red Blood Cells (RBC) | Cells/µL | On samples <1500 cells/µL |
| Mononuclear (MN) cells | Cells/µL | On samples >20 cells/µL |
| Polymorphonuclear (PMN) cells | Cells/µL | On samples >20 cells/µL |
| Neutrophils | Cells/µL | On samples >20 cells/µL |
| Lymphocytes | Cells/µL | On samples >20 cells/µL |
| Monocytes | Cells/µL | On samples >20 cells/µL |
| Eosinophils | Cells/µL | On samples >20 cells/µL |
| Mononuclear (MN) cells, MN % | % of WBC | On samples >20 cells/µL |
| Polymorphonuclear (PMN) cells, PMN % | % of WBC | On samples >20 cells/µL |
| Neutrophils, Neut % | % of WBC | On samples >20 cells/µL |
| Lymphocytes, Lymph % | % of WBC | On samples >20 cells/µL |
| Monocytes, Mono % | % of WBC | On samples >20 cells/µL |
| Eosinophils, Eos % | % of WBC | On samples >20 cells/µL |

In the semi-automated CSF method, the analyzer performs a WBC count, RBC count, and 4-part WBC differential on CSF samples. The method allows sample throughput for up to 120 samples per hour.

The present semi-automated method for the analysis of body fluids affords numerous advantages in assay performance and for the customer. Automation of the assay of body fluids such as CSF provides results that are obtained significantly faster than those which are obtained using manual methods. For instance, while the semi-automated assay results according to the present invention are provided at a rate of about 60 to 120 samples per hour, completely manual assay results are provided at a rate of 1 to 2 samples per hour.

In addition, the semi-automated method requires less operator skill than is required for manual cell counting. There is a faster turnaround time for cell counts, differential percentages and absolute counts, since these values and parameters are automatically calculated. The end user benefits from the reduction of labor, cost of materials, improved laboratory efficiency and decreased turnaround time. In addition, the method affords increased accuracy and precision of patient results; patient results can be reported more quickly to the physician. Labor time is also reduced, e.g., by at least about 20 minutes per sample.

Another aspect of the present invention encompasses a CSF assay test kit or test kit for the assay of other body fluids. Preferably, the CSF kit includes a reagent bottle comprising the reagent composition according to the present invention for a set number of cycle determinations, and, optionally, but preferably, a smart card, bar code or key that permits software access to process CSF samples or controls on an automated analyzer instrument. The test kit is preferably packaged with sufficient volume of the reagent composition for about 25 CSF tests, for example, for the processing of both control samples and/or patient CSF samples.

A CSF control can be part of the test kit; alternatively, the control can comprise a separate kit. For the CSF control, preferably a control kit that is separate from the test kit, a two cell count-level, value-assigned CSF control product is included. The two cell count control comprises two cell count levels: a high control with approximately 100 WBC/μL and a low control with approximately 10 WBC/μL. The CSF control also preferably comprises the reagent composition according to the present invention.

CSF control products further preferably contain a readable (by the operator) package insert that provides the lot number, target values, acceptable ranges and expiration date, etc., for each parameter and each level. Also embraced by the invention is bar-coded information so that the user can scan the barcode with the system's barcode reader; thereafter, the appropriate values (e.g., target values, ranges, etc.) are automatically entered into the QC files of the analyzer. Also preferably included in the kit(s) are instructions for use.

The CSF assay of the present invention, preferably performed using an ADVIA 120® automated analyzer, provides both clinical and relative accuracy. The ADVIA 120® WBC count in CSF samples is compared to reference manual counts. Normal samples are defined as samples with approximately 0-5 WBC cells/μL; abnormal samples are typically defined as samples with approximately >5 WBC cells/μL. A study with 54 normal samples and 26 abnormal CSF samples, as determined by reference methods, showed that the ADVIA 120® instrument has a sensitivity of ≧95% and a specificity of ≧85% (Example 5). It will be appreciated that because of the very small numbers of cells counted in many of the samples, especially the reference manual counts, for statistical reasons only, the performance of the assay is considered optimal.

EXAMPLES

The following examples describe specific aspects of the invention to illustrate the invention and provide a description of the present methods for those of skill in the art. The examples should not be construed as limiting the invention, as the examples merely provide specific methodology useful in understanding and practice of the invention and its various aspects.

Example 1

Analysis of CSF Samples According to the Present Invention

Figures 11A, 11B:
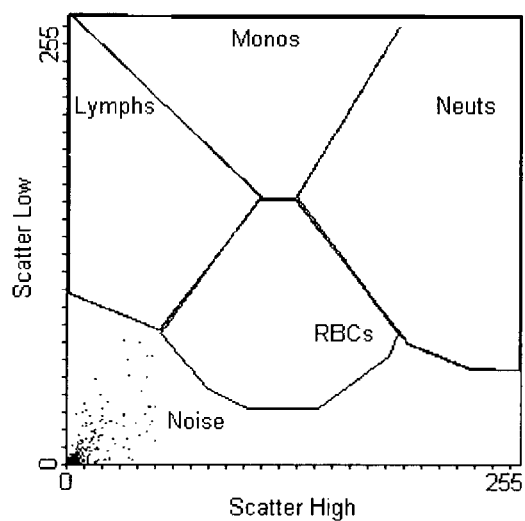
FIGS. 11A-11H illustrate the results from the analysis of 5 CSF samples obtained from a hospital laboratory, as described in Example 1.
Figures 11C, 11D:
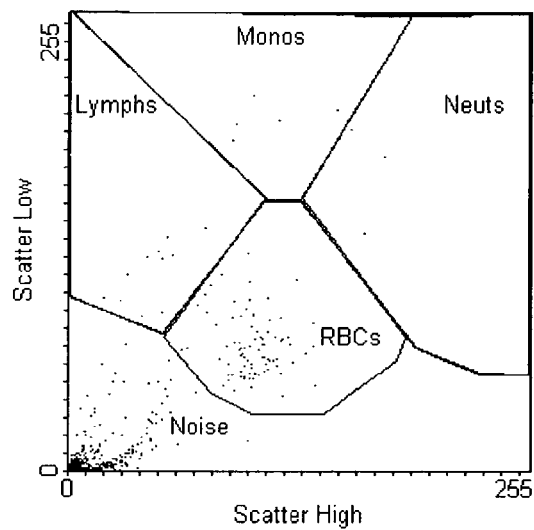
Figures 11E, 11F:
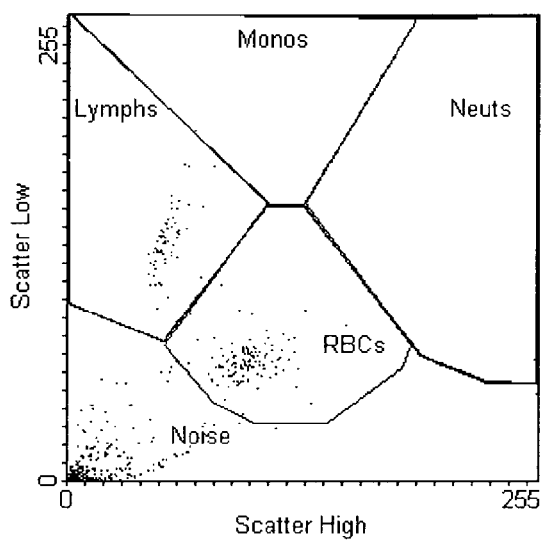
Figures 11G, 11H:
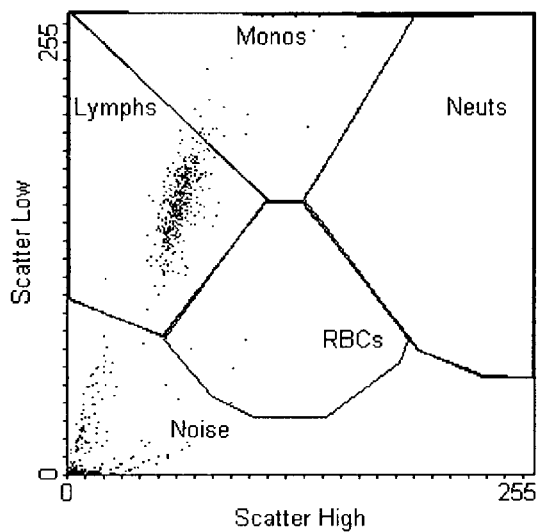

The cytograms shown in FIGS. 11A-H represent the results from the analysis of CSF samples obtained from a hospital laboratory. The samples were less than two hours old when received for analysis. CSF samples were prepared by adding 0.5 mL of sample to 0.5 mL of CSF reagent according to the present invention. The sample and reagent composition mixture was incubated for 5 minutes at room temperature and aspirated onto an ADVIA 120® automated analyzer in direct cytometry mode. Raw data files from sample acquisitions were converted into Flow Cytometry Standard (FCS) format and analyzed offline using WinMDI software. FIG. 11A shows the results of the analysis of a normal, nearly acellular CSF sample; FIG. 11B presents ADVIA 120® automated and reference manual CSF results related to FIG. 11A; FIG. 11C shows the results of the analysis of a sample with low WBC counts; FIG. 11D presents ADVIA 1200 automated and reference manual CSF results related to FIG. 11C; FIG. 11E shows the results of the analysis of a sample containing WBC at a level of approximately 20 WBC; FIG. 11F presents ADVIA 120® automated and reference manual CSF results related to FIG. 11E; FIG. 11G shows the results of the analysis of a sample at the level of approximately 100 WBC/μL; and FIG. 11H presents ADVIA 120® automated and reference manual CSF results related to FIG. 11G. A comparison of automated and manual values shows good agreement between the two methods.

Example 2

Accuracy Results

Data obtained using the method of the present invention and the ADVIA 120® automated analyzer were compared with reference manual values for 80 CSF sample acquisitions. Table 4 below summarizes the regression statistics for the comparison of absolute RBC, WBC and WBC differential values obtained for the 80 CSF samples. All CSF samples were prepared as follows: CSF samples were prepared by adding 0.5 mL of sample to 0.5 mL of CSF reagent of this invention; the sample and reagent mixture was incubated for 5 minutes at room temperature and aspirated onto the ADVIA 120® analyzer in direct cytometry mode. Raw data files from sample acquisitions were converted into Flow Cytometry Standard (FCS) format and analyzed offline using WinMDI software.

TABLE 4

| Parameter | Manual Mean | ADVIA 120® Mean | Δ | % Bias | Syx | Slope | Intercept | r |
|---|---|---|---|---|---|---|---|---|
| # WBC | 34 | 37 | 3 | −9 | 11.9 | 1.04 | 1 | 0.99 |
| # RBC | 133 | 136 | 4* | −3 | 94.9 | 1.07 | −6 | 0.97 |
| # Neuts | 4 | 3 | 1 | 25 | 3 | 0.75 | 1 | 0.94 |
| # Lymphs | 19 | 26 | 7 | −36 | 12 | 1.37 | −1 | 0.99 |
| # Monos | 11 | 8 | 3 | 27 | 7 | 0.72 | 0 | 0.97 |

TABLE 4-continued

| Parameter | Manual Mean | ADVIA 120® Mean | Δ | % Bias | Syx | Slope | Intercept | r |
|---|---|---|---|---|---|---|---|---|
| # Eos | 0 | 0 | 0 | 0 | NA | NA | NA | NA |
| # MN | 30 | 34 | 4 | −13 | 17.8 | 1.09 | 1 | 0.98 |
| # PMN | 4 | 3 | 1 | 25 | 3 | 0.75 | 1 | 0.94 |

*RBC values rounded up; NA: Not available.
Syx, the "standard error of estimate" is the degree to which data points cluster around the regression line. The closer the points are to the line, the smaller the standard error of estimate, and the better the agreement between the two methods being compared.

Figure 4:
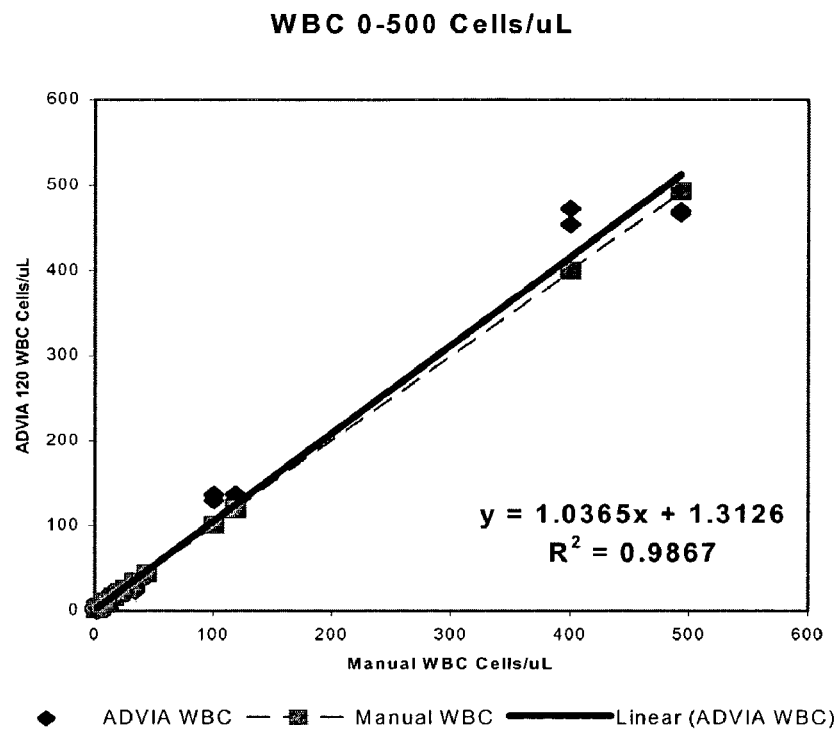
FIG. 4 presents WBC results and shows the correlation of CSF assay results according to the present invention performed on an ADVIA 120® analyzer versus manual analysis results of WBC counts for 80 CSF samples.

FIG. 4 presents WBC results obtained from the experiments described in this example and shows the correlation of CSF assay results according to the present invention performed on an ADVIA 120® analyzer versus manual analysis results of WBC counts for the 80 CSF samples. For FIG. 4 and those described below, all CSF samples were prepared as described above.

Figure 5:
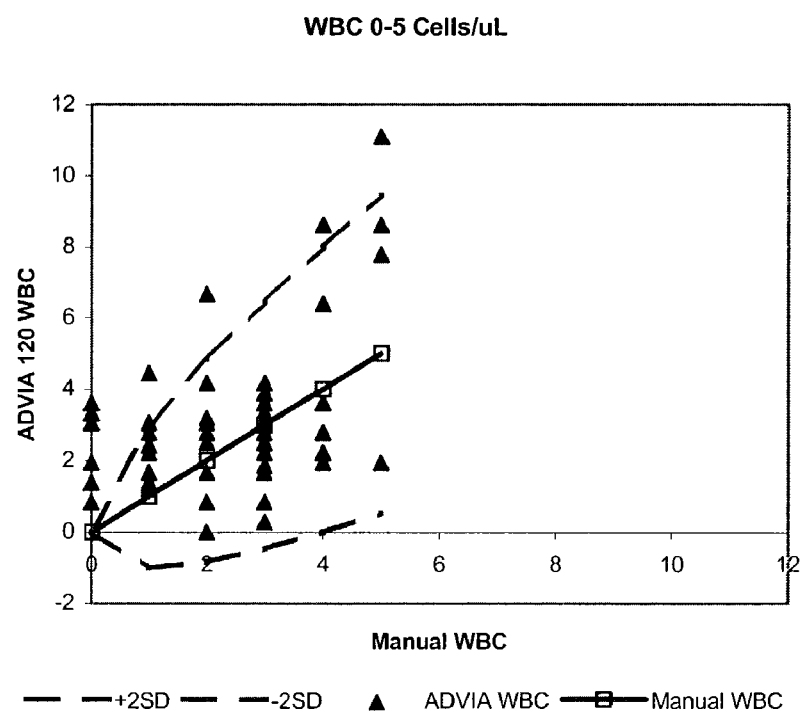
FIG. 5 shows the correlation of CSF assay results according to the present invention performed on an ADVIA 120® analyzer versus manual analysis results of WBC counts for 52 CSF samples with WBC counts having ≦5 cells/μL and showing ±2 SD to reflect the imprecision of the manual result.

FIG. 5 shows the correlation plot of CSF assay results obtained from the experiments described in this example according to the present invention performed on an ADVIA 120® analyzer versus the results of manual analysis of WBC counts for samples with WBC counts having ≦5 cells/μL and showing ±2 SD to reflect the imprecision of such low counts for 52 CSF samples.

Figure 6:
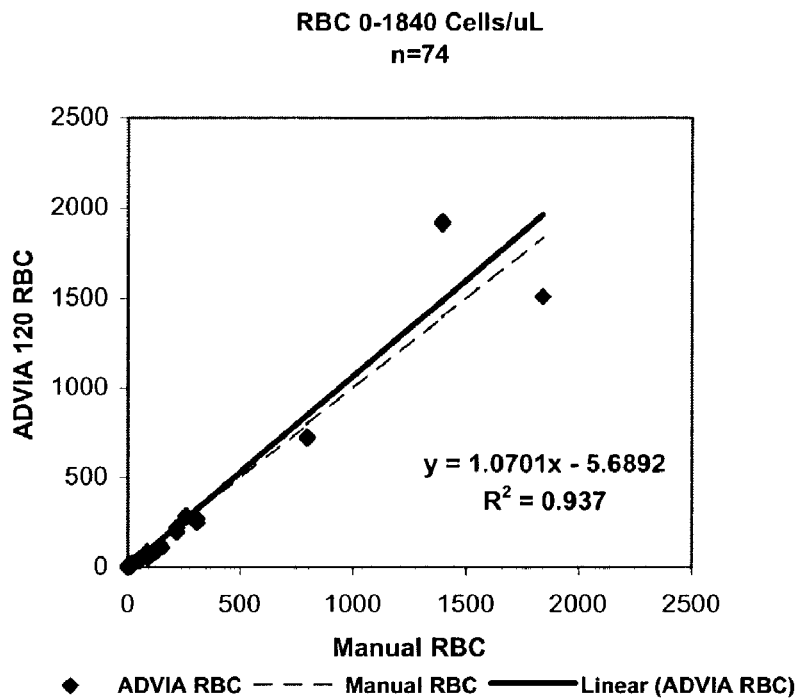
FIG. 6 shows the correlation of CSF assay results according to the present invention performed on an ADVIA 120® analyzer versus manual analysis results for RBC counts between 0 and 1840 in 74 CSF samples.

FIG. 6 shows the correlation plot of CSF assay results obtained from the experiments described in this example according to the present invention performed on an ADVIA 120® analyzer versus the results of manual analysis for RBC counts between 0 and 1840 in 74 CSF samples.

Figure 7:
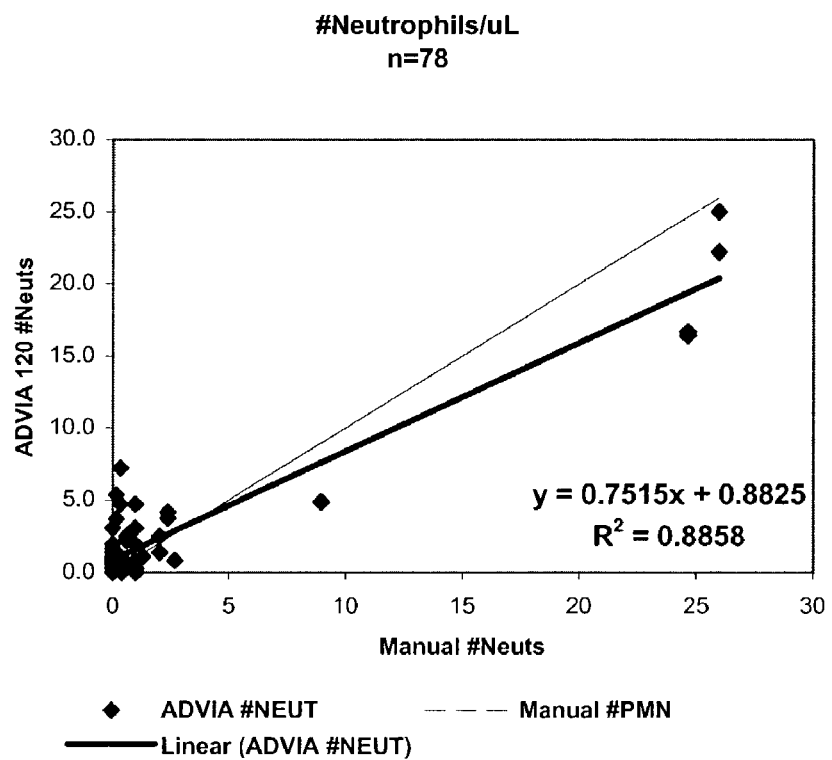
FIG. 7 shows the correlation of CSF assay results according to the present invention performed on an ADVIA 120® analyzer versus manual analysis results for the number of neutrophils in 78 CSF samples. Since the samples in this study did not contain sufficient eosinophils to reliably differentiate them from neutrophils, the FIG. 7 graph represents only the total number of polymorphonuclear cells (i.e. neutrophils (NEUTS) plus eosinophils (EOS)).

FIG. 7 shows the correlation plot of CSF assay results obtained from the experiments described in this example according to the present invention performed on an ADVIA 120® analyzer versus the results of manual analysis for the number of neutrophils in 78 CSF samples. Since the samples in this study did not contain sufficient eosinophils to distinguish them from neutrophils, this graph represents the total number of polymorphonuclear (PMN) cells.

Figure 8:
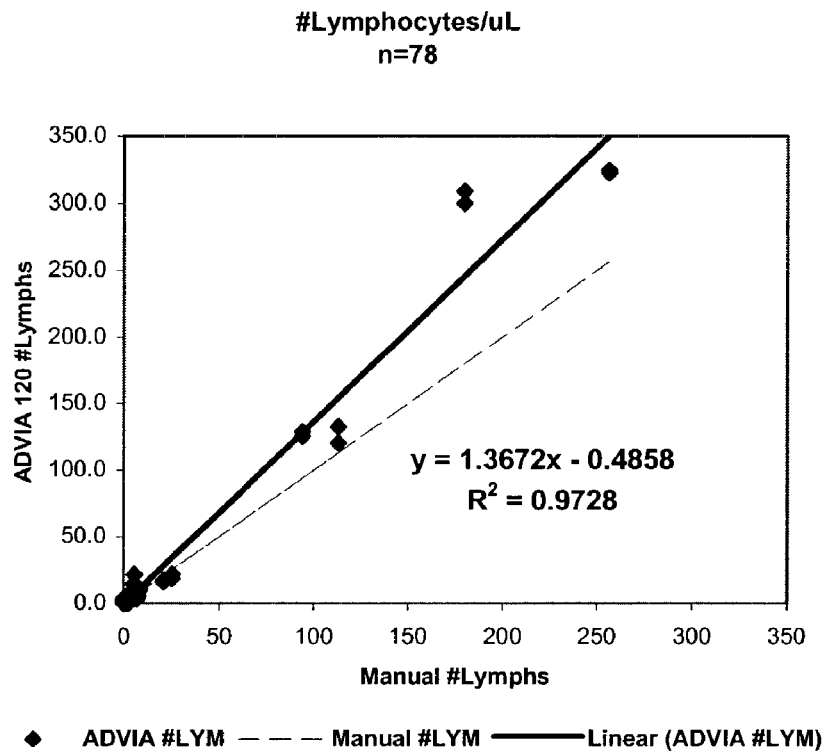
FIG. 8 shows the correlation of CSF assay results according to the present invention performed on an ADVIA 120® analyzer versus manual analysis results for the number of lymphocytes in 78 CSF samples.

FIG. 8 shows the correlation plot of CSF assay results obtained from the experiments described in this example according to the present invention performed on an ADVIA 120® analyzer versus the results of manual analysis for the number of lymphocytes in 78 CSF samples.

Figure 9:
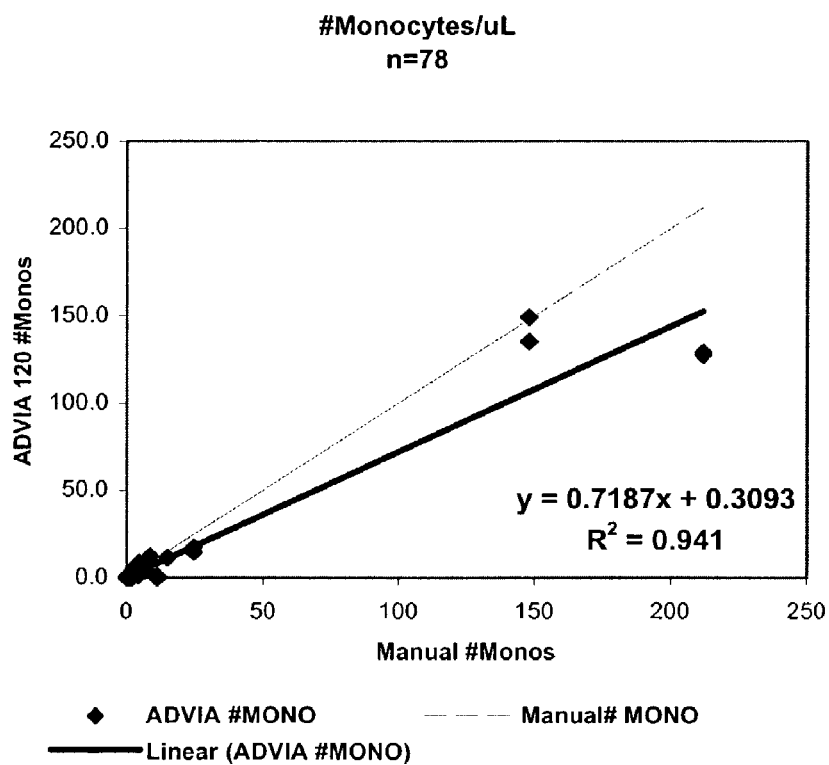
FIG. 9 shows the correlation of CSF assay results according to the present invention performed on an ADVIA 120® analyzer versus manual analysis results for the number of monocytes in 78 CSF samples.

FIG. 9 shows the correlation plot of CSF assay results obtained from the experiments described in this example results according to the present invention performed on an ADVIA 120® analyzer versus the results of manual analysis for the number of monocytes in 78 CSF samples.

Figure 10:
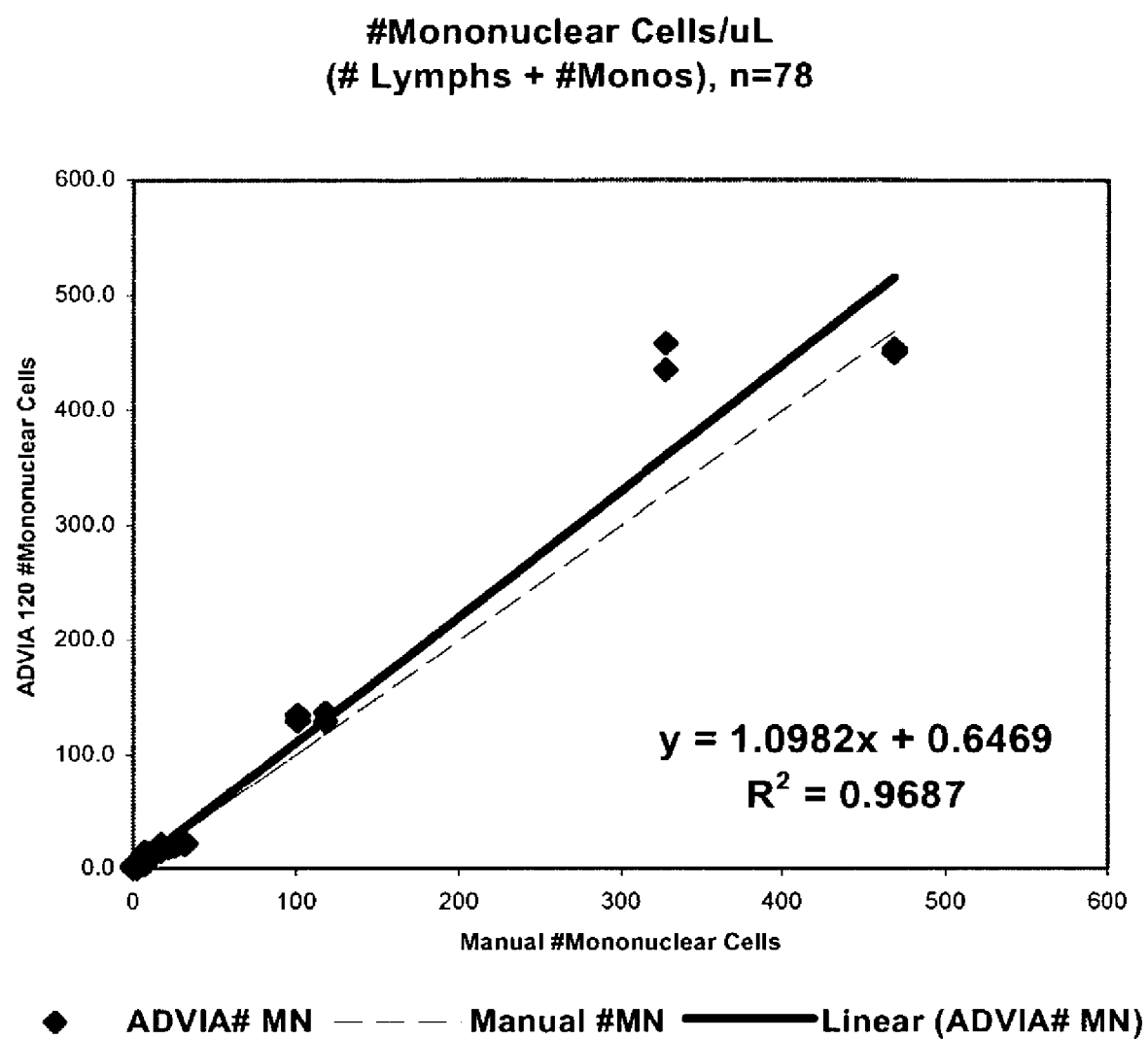
FIG. 10 shows the correlation of CSF assay results according to the present invention performed on an ADVIA 120® analyzer versus manual analysis results for the number of mononuclear cells in 78 CSF samples.

FIG. 10 shows the correlation plot of CSF assay results obtained from the experiments described in this example according to the present invention performed on an ADVIA 120® analyzer versus the results of manual analysis for the number of mononuclear (MN) cells (lymphocytes plus monocytes) in 78 CSF samples.

Example 3

Precision Results

This example presents precision results obtained from thirty-one hospital CSF samples acquired in duplicate using the method of the present invention performed on an ADVIA 120® automated analyzer. The samples were evaluated for reproducibility using the following formula:

$$[(\Sigma \Delta^2)/2n]^{1/2}$$

where: $\Sigma \Delta$ is the sum of the differences between sample duplicates and n is the number of samples. The standard deviation (SD) and % CV (coefficient of variation, (100×(SD/Mean)) were calculated for WBC, RBC, PMN and MN cell counts and are presented in Table 5:

TABLE 5

| | CSF Results | | |
|---|---|---|---|
| Parameter | Average n = 31 | SD | % CV |
| WBC | 46 | 2.88 | 6.29 |
| RBC | 180 | 7.79 | 4.41 |
| #MN | 43 | 3.42 | 0 |
| #PMN | 3 | 0.8 | 0 |

Example 4

Linearity Results

A linearity pool of 0%, 0.05%, 0.1%, 0.2%, 1%, 10% and 100% was made from a platelet rich plasma sample. These samples were diluted 1:1 in CSF reagent and run on the ADVIA 120® cytometry analyzer in direct cytometry mode. Table 6A presents the measured versus expected WBC and RBC values of five replicates resulting from the analysis described in this example. The results were within linearity specifications for maximum deviations as shown in Table 6B.

TABLE 6A

| | WBC Linearity | | | | RBC Linearity | | | |
|---|---|---|---|---|---|---|---|---|
| Level | Observed Cells/μL | Expected Cells/μL | Diff | % Diff | Observed Cells/μL | Expected Cells/μL | Diff | % Diff |
| 0.00% | 0 | 0 | 0 | | 0 | 0 | 0 | |
| 0.05% | 4 | 3 | 1 | | 1 | 1 | 0 | |
| 0.10% | 6 | 7 | −1 | | 2 | 3 | −1 | |
| 0.20% | 12 | 13 | −1 | | 5 | 6 | 0 | |
| 1% | 64 | 67 | | 4.5% | 24 | 26 | −2 | |
| 10% | 660 | 674 | | 2.1% | 274 | 261 | | 5.0% |
| 100% | 6739 | 6739 | | 0.0% | 2610 | 2610 | | 0.0% |

TABLE 6B

Linearity Specifications

| Parameter | Linear Range (cells/μL) | Maximum Deviation |
|---|---|---|
| WBC | 0-50 | 5 cells |
|  | 50-5000 | 10% |
| RBC | 0-50 | 5 cells |
|  | 50-5000 | 10% |

Figure 12A:
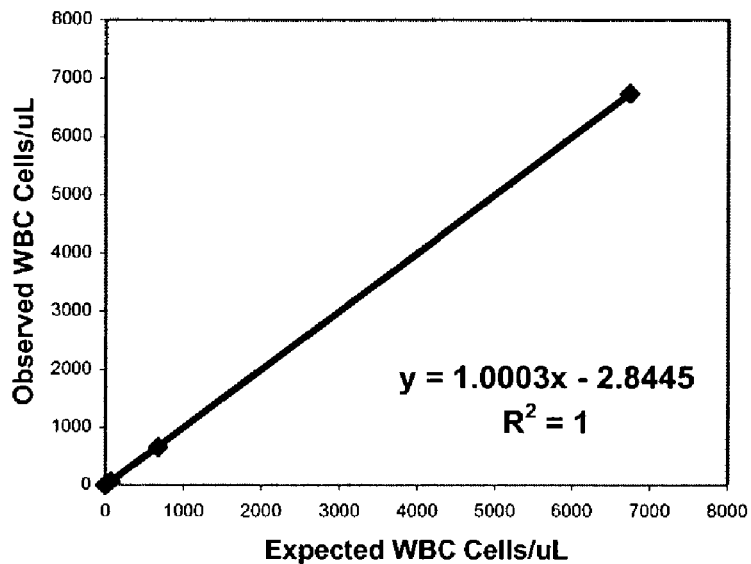
FIGS. 12A and 12B illustrate a regression analysis for WBC (FIG. 12A) and RBC (FIG. 12B), as described in Example 4. The experimentally obtained (observed) cell numbers are identical to the expected values for white cells and red cells.
Figure 12B:
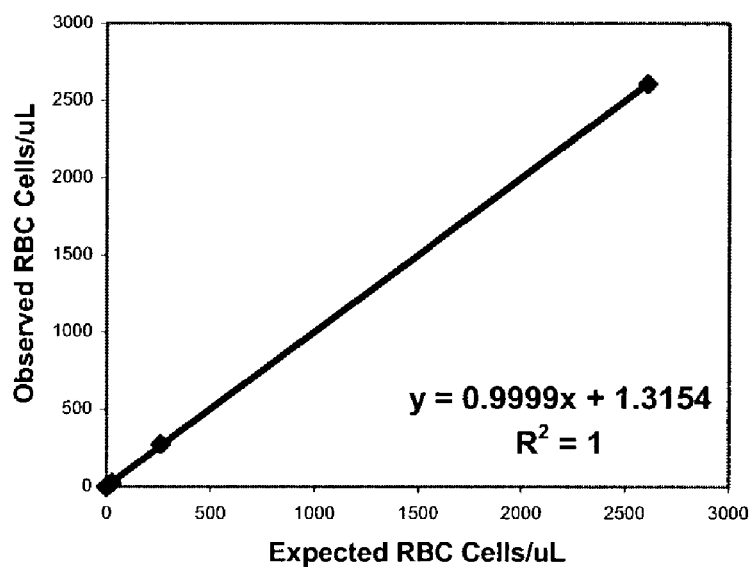

FIGS. 12A and 12B present regression analysis results for WBC (FIG. 12A) and RBC (FIG. 12B). As determined, the experimentally obtained (observed) cell numbers are identical to expected values for white cells and red cells.

Example 5

Clinical Sensitivity and Specificity

Clinical sensitivity and specificity were calculated using truth table analysis for WBC counts in which a value of >5 WBC cells/μL was considered positive. Table 7 shows a schematic for evaluating samples with respect to distributional classification. Table 8 shows the distribution of 80 CSF samples that were analyzed using automated and reference manual methods. The presence of >5 WBC/μL classified a sample as abnormal. Results of the method comparison are shown in Table 9. Statistics derived from sample distribution indicate good agreement between the two methods. Seven samples were classified as false positives in this comparison (Table 7), which could be explained by the following: the automated method counts a higher volume of sample and more cells than the manual method and is therefore more precise than the manual method in detecting cellular events.

TABLE 7

| Manual Differential | ADVIA 120 ® (Test Method Result) | |
|---|---|---|
| (Reference Method Result) | Abnormal (Pos) (+) | Normal (Neg) (−) |
| Abnormal (Pos) (+) | TP | FN |
| Normal (Neg) (−) | FP | TN |

In the above Table 7:
TP (True Positive) = number of samples both methods agree were abnormal
TN (True Negative) = number of samples both methods agree were normal
FN (False Negative) = number of samples deemed abnormal by reference method and normal by test method
FP (False Positive) = number of samples deemed normal by reference method and abnormal by test method Truth Table Calculations
   Agreement Rate=(TP+TN)/(TP+TN+FP+FN)×100%
   False Negative Rate=FN/(FN+TP)×100%
   False Positive Rate=FP/(FP+TN)×100%
   Sensitivity %=(100−FN rate)=the rate of correct decisions in samples with abnormality
   Specificity %=(100−FP rate)=the rate of correct decisions in samples without abnormality

TABLE 8

Truth Table Results

| CSF Analysis | TP | TN | FP | FN | # Samples with >5 WBC cells/μL | Total # samples |
|---|---|---|---|---|---|---|
| ADVIA 120 ® | 25 | 47 | 7 | 1 | 26 | 80 |

TABLE 9

| CSF Analysis: ADVIA 120 ® Method versus Manual Method | |
|---|---|
| Agreement Rate | 90(%) |
| False Negative Rate | 4(%) |
| False Positive Rate | 13(%) |
| Sensitivity | 96(%) |
| Specificity | 87(%) |
| Pos Pred. Value | 78(%) |
| Neg Pred Value | 98(%) |

The above percentages in Table 9 above indicate how frequently an analysis involving such small numbers of cells leads to correct results, i.e., true positive (TP) or true negative (TN) results, or to incorrect results, i.e., false positive (FP) or false negative (FN) results, due to statistical sampling error.

The contents of all issued and granted patents, patent applications, published PCT and U.S. applications, articles, books, references, reference manuals and abstracts as referenced or cited herein are hereby incorporated by reference in their entireties to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. An automated method for the analysis of a non-blood body fluid, comprising: (a) mixing an aliquot of the body fluid with a reagent composition comprising, in aqueous solution, at least one aldehyde, at least one surface-active agent and cyclodextrin to form a reagent mixture to prevent leakage from cells; (b) aspirating the reagent mixture into an automated analyzer; (c) analyzing the components in the reagent mixture virtually one cell at a time by direct cytometry; and (d) obtaining counts of cell components and cell-by-cell volumes and dry-mass concentrations of the cell components in the body fluid using said direct cytometry.

2. The method according to claim 1, further comprising: obtaining a cytogram of the cell components in the body fluid.

3. The method according to claim 1, wherein the method is semi-automated or fully-automated.

4. The method according to claim 1, wherein the method is semi-automated.

5. The method according to claim 1, wherein the body fluid is selected from the group consisting of cerebrospinal fluid (CSF), pleural fluid, pulmonary lavage fluid, bronchial lavage fluid, synovial fluid, peritoneal fluid, bone marrow aspirate fluid, ascites fluid, sputum, saliva, lymph, tears, serum, plasma, semen, urine, and bladder wash.

6. The method according to claim 5, wherein the body fluid is cerebrospinal fluid (CSF).

7. The method according to claim 1, wherein the at least one aldehyde in the reagent composition is glutaraldehyde, formaldehyde, or a combination of glutaraldehyde and formaldehyde.

8. The method according to claim 7, wherein the surface active agent is a zwitterionic surfactant.

9. The method according to claim 1, wherein the surface active agent is a zwitterionic surfactant.

10. The method according to claim 9, wherein the zwitterionic surfactant is selected from the group consisting of betaines, alkylbetaines, carboxybetaines, sulfobetaines, amidobetaines and sulfoamidobetaines.

11. The method according to claim 10, wherein the sulfobetaine is selected from the group consisting of n-alkyl dimethylammonio methane sulfonate (DAMS), n-alkyl dimethylammonio ethane sulfonate (DABS), n-alkyl dimethylammonio propane sulfonate (DAPS), n-alkyl dimethylammonio butane sulfonate (DABS), n-tetradecyl dimethylammonio propane sulfonate (TDAPS), and dodecyl dimethylammonio propane sulfonate (DDAPS).

12. The method according to claim 9, wherein the zwitterionic surfactant is n-tetradecyl dimethylammonio propane sulfonate (TDAPS).

13. The method according to claim 9, wherein the zwitterionic surfactant is 3-[3-cholamidopropyl)dimethylammonio]-1-propanesulfonate (CHAPS) or 3-[(3-cholamidopropyl)dimethylammonio]-2-hydroxy-1-propanesulfonate (CHAPSO).

14. The method according to claim 1, wherein the surface active agent is a nonionic surfactant.

15. The method according to claim 7, wherein the surface active agent is a nonionic surfactant.

16. The method according to claim 14, wherein the nonionic surfactant is an alkylglycoside.

17. The method according to claim 16, wherein the alkylglycoside nonionic surfactant is selected from the group consisting of n-dodecyl-β-D-maltoside, n-tetradecyl-β-D-maltoside and n-tetradecyl-β-D-glucoside.

18. The method according claim 1, wherein the surface active agent is present in the composition in an amount of from about 1.5 g/L to about 3 g/L.

19. The method according to claim 1, wherein the surface active agent is present in the composition in an amount of from about 1.8 g/L to about 2.5 g/L.

20. The method according to claim 1, wherein the cyclodextrin is selected from alpha (α) cyclodextrin, beta (β) cyclodextrin, or gamma (γ) cyclodextrin.

21. The method according claim 1, wherein the cyclodextrin is hydroxypropyl-β-cyclodextrin.

22. The method according to claim 1, wherein the cyclodextrin is present in the composition in an amount of from about 10 g/L to about 35 g/L.

23. The method according to claim 1, wherein the cyclodextrin is present in the composition in an amount of from about 15 g/L to about 21 g/L.

24. The method according to claim 1, wherein the reagent composition further comprises a buffering agent to maintain reagent pH in the range of about pH 4.0 to pH 7.0.

25. The method according to claim 24, wherein the pH of the reagent composition is in the range of about pH 4.5 to pH 6.0.

26. The method according to claim 24, wherein the buffering agent comprises one or more of $Na_2HPO_4$ and/or $NaH_2PO_4$, citric acid and its salts, succinic acid and its salts, and ethylene diamene tetra acetic acid (EDTA) and its salts.

27. The method according to claim 7, wherein formaldehyde is present in the reagent composition in an amount of from about 10 g/L to about 25 g/L, and glutaraldehyde is present in the reagent composition in an amount of from about 1 g/L to about 5 g/L.

28. The method according to claim 7, wherein formaldehyde is present in the reagent composition in an amount of from about 15 g/L to about 23 g/L, and glutaraldehyde is present in the reagent composition in an amount of from about 2 g/L to about 3 g/L.

29. The method according to claim 7, wherein formaldehyde is present in the reagent composition in an amount of from about 18 g/L to about 21 g/L, and glutaraldehyde is present in the reagent composition in an amount of from about 2.4 g/L to about 2.6 g/L.

\* \* \* \* \*